United States Patent [19]

Watanabe

[11] Patent Number: 4,925,939
[45] Date of Patent: May 15, 1990

[54] 6,7-DIHYDROPYRROL[3,4-C]PYRIDO[2,3-D]PYRIMIDINE DERIVATIVES

[75] Inventor: Kyoichi A. Watanabe, Rye-Brook

[73] Assignee: Sloan-Kettering Institute for Cancer Research, New York, N.Y.

[21] Appl. No.: 293,940

[22] Filed: Jan. 5, 1989

[51] Int. Cl.$^5$ ............... C07D 239/000; C07D 487/00
[52] U.S. Cl. .................................. 544/251; 544/250
[58] Field of Search ............................... 544/250, 251

[56] References Cited

U.S. PATENT DOCUMENTS 2,594,271  4/1952  Fahrenbach ..................... 544/251
4,118,561  10/1978  Lodig .............................. 544/250

OTHER PUBLICATIONS

Ganglee, et al., J. Heterocyclic Chemistry, 24(1), 1987, pp. 123 & 126.

Primary Examiner—Mukund J. Shah
Assistant Examiner—Edward Ward
Attorney, Agent, or Firm—John P. White

[57] ABSTRACT

The present invention concerns compounds of the formula:

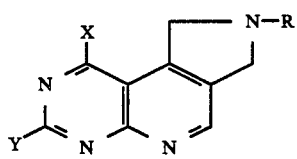

wherein R is a lower alkyl group, an aryl group or an alkylaryl group and X and Y are the same or different, and each is OH, $NH_2$, or SH. The aryl group or the aryl moiety of the alkylaryl group may be unsubstituted, monosubstituted, disubstituted or trisubstituted. If substituted, each substituent may independently be an alkyl group, an alkyloxy group or a halogen.

The present invention also provides methods for synthesizing the compounds described above.

5 Claims, 4 Drawing Sheets

1

2

3a  X = OH,  R = 2,5-dimethoxyphenyl
3b  X = $NH_2$,  R = 4-methoxyphenyl

6,7-DIHYDROPYRROL[3,4-C]PYRIDO[2,3-D]PYRIMIDINE DERIVATIVES

The invention described herein was made in the course of work under Grant Nos. 2-P01-CA-18856 CA-08748 from the National Cancer Institute, National Institutes of Health, U.S. Department of Health and Human Services. The U.S. Government has certain rights in this invention.

BACKGROUND OF THE INVENTION

The tricyclic 6,7-dihydro[3,4-c]pyrido[2,3-d]pyrimidine ring system has been the subject of intensive studies because such ring system is structurally very close to the key skeleton of 5,10-methylenetetrahydrofolic acid which donates one carbon unit to 2'-deoxyuridylic acid to produce thymidylic acid during the de novo synthesis of DNA.

For normal or neoplastic cell growth or cell division, DNA must be synthesized. During the synthesis of DNA, folic acid is converted into its active form, 5,10-methylenetetrahydrofolic acid, which then methylate 2'-deoxyuridylate to produce thymidyate, a building block in the snythesis of DNA. Methotrexate and other folic acid analogues block the formation of 5,10-methylenetetrahydrofolic acid and thereby produce a "starvation" of thymidylate and an inhibition of DNA synthesis.

No successful synthesis of the tricyclic 6,7-dihydro[3,4-c]pyrido[2,3-dpyrimidine ring system has been reported. This invention deals with the first synthesis of the tricyclic derivatives by two different routes: one by construction of the pyrimidine ring on the 2,3-dihydropyrrolo[3,4-c]pyridine system and the other by addition of the 5-membered pyrrolidine ring to the preformed pyrido[2,3-d]pyrimidine ring system.

The derivatives of this invention may interfere with thymidylate synthesis from 2'-deoxyuridylate. Since the derivatives of the subject invention resemble structurally 5,10-methylenetetrahydrofolic acid, they may react with methylene tetrahydrofolate cyclase. The compounds of the subject invention may also react with 2'-deoxyuridylate in the active site of thymidylate synthase to form an enzyme substrate complex in which the complex can not release the product. Accordingly, the derivatives of the subject invention may be useful as biochemical probes for biological reactions essential for DNA synthesis.

The derivatives of this invention may also be useful as potential anticancer agents since they inhibit DNA synthesis at the thymidylate level. In the same manner as several folic acid analogues, such as methotrexate, 10-deaza-10-ethyl-methotrexate or aminopterin, the derivatives of the present invention may inhibit thymidylate formation and thus DNA synthesis.

SUMMARY OF THE INVENTION

The present invention concerns compounds of the formula:

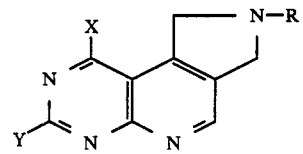

wherein R is a lower alkyl group, an aryl group or an alkylaryl group and X and Y are the same or different, and each is OH, $NH_2$, or SH. The aryl group or the aryl moiety of the alkylaryl group may be unsubstituted, monosubstituted, disubstituted or trisubstituted. If substituted, each substituent may independently be an alkyl group, an alkyloxy group or a halogen.

The present invention also provides methods for synthesizing the compounds described above.

DETAILED DESCRIPTION OF THE INVENTION

Figure 1:
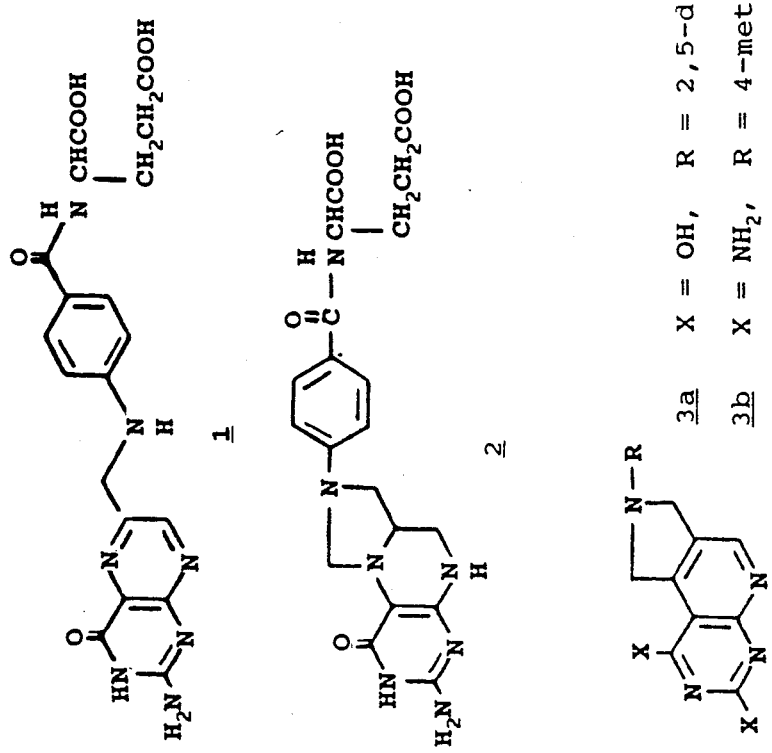
FIG. 1: Structures of folic acid (Compound 1), 5,10-methylene tetrahydrofolic acid (Compound 2), and two 6,7-dihydropyrrolo[3,4-c]pyrido[2,3-d]pyrimidines (Compounds 3a and 3b).

The present invention provides compounds and synthesis methods for compounds which contain the 6,7-dihydro-pyrrolo[3,4-c]pyrido[2,3-d]-pyrimidine ring system. These compounds may be represented by the formula:

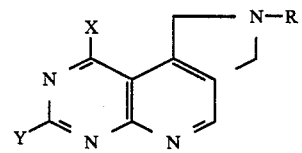

Formula I wherein R is a lower alkyl group, an aryl group or an alkylaryl group and X and Y are the same or different, and each is OH, $NH_2$, or SH. The aryl group or the aryl moiety of the alkylaryl group may be unsubstituted, monosubstituted, disubstituted or trisubstituted. If substituted, each substituent may independently be an alkyl group, an alkyloxy group or a halogen, an wherein X and Y are the same or different and each is OH, $NH_2$, or SH.

In the preferred embodiments of the inventions, suitable lower alkyl groups are those groups having from one to about seven carbon atoms, such as methyl, ethyl, propyl, butyl, pentyl or hexyl groups. The lower alkyl group may be a straight or branched chain and may have one or more substituents for the hydrogens attached to the carbon atoms. Suitable aryl groups include phenyl, benzyl, methoxyphenyl, methoxybenzyl, and naphthyl groups. The term "alkylaryl" refers to groups having an alkyl moiety attached to an aryl ring, such as a phenyl or benzyl ring. The alkyl moiety is preferably a lower alkyl chain, from one to seven carbon atoms in length. The alkyl moiety may also contain oxygen, nitrogen or sulfur atoms, such as methoxy moiety. Presently preferred alkylaryl groups are methylphenyl, methoxyphenyl, methylbenzyl and methoxybenzyl groups.

The aryl group or the aryl moiety of the alkylaryl group may be unsubstituted, monosubstituted, disubstituted or trisubstituted. If substituted, each substituent may independently be a lower alkyl group (e.g. a group having 1 to 7 carbon atoms), an alkyloxy group (preferably, methoxy) or a halogen (preferably, fluorine, chlorine, or bromine).

In the embodiments where X and Y are OH groups, it is intended that the enol form of the compound be equivalent to, an include, the keto form of the compound. That is, it is intended that the compound of the structure:

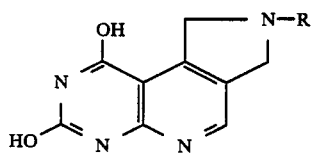

include and is equivalent to compounds of the structure:

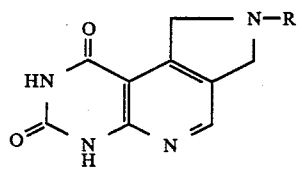

The invention also provides methods of synthesizing the compounds. The first synthesis preferably begins with reaction of alkylamines, substituted arylalkylamines or substituted arylamines with alkyl acrylate to give N-substituted b-aminopropionate of formula II:

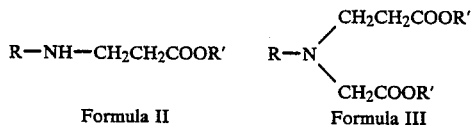

Formula II     Formula III wherein R is a lower alkyl group, preferably of 1–7 carbons, an aryl group or alkylaryl group with an unsubstituted, monosubstituted, disubstituted, or trisubstituted phenyl ring; each substituent on the phenyl ring preferably is a methyl group, a methoxy group or a halogen, preferably fluorine, chlorine or bromine. R' is a lower alkyl group, preferably of 1–7 carbons, or a phenyl group.

The reaction is carried out in alcohol (such as methanol, ethanol, or isopropanol) with or without acid catalyst (an organic acid such as acetic acid, chloroacetic acid, fluoroacetic acid, p-toluenesulfonic acid, and the like or inorganic acid such as phosphoric acid, sulfuric acid and the like) the reaction may also be carried out in acetic acid at a temperature from 20° C. to 118° C. (boiling temperature of acetic acid) for a period of 30 minutes to one week.

Alkylation of compounds of formula II with an alkyl haloacetate, preferably ethyl bromoacetate, in a polar solvent such as methyl or ethyl alcohol, N,N-dimethylformamide, dimethylsulfoxide or hexamethylphosphoric triamide in the presence of a base, preferably potassium carbonate, at a temperature from about 40° C. to 120° C. for a period of from 2 to 24 hours affords the corresponding N,N-disubstituted glycine derivatives of formula III.

Compounds of formula III are then coverted into 1-substituted 4-ethoxycarbonylpyrrolidine-3-one of formula IV by intramolecular Dieckmann reaction. The reaction may proceed in an aromatic hydrocarbon (such as benzene and toluene), alcohol (such as methanol, ethanol and the like), or in a mixture of aromatic hydrocarbon and alcohol, in the presence of the corresponding alkoxide of alkali metal (such as lithium, sodium or potassium) at a temperature range of from 25° C. to 97° C. (boiling temperature of propanol) for a period of from 30 minute to 4 hours.

Saponification of compounds of formula IV with simultaneous decarboxylation of the product gives the compounds of formula V. Formation of compounds of formula V can be achieved by treatment of compounds of formula IV with an acid, such as acetic acid or hydrochloric acid of various normality (e.g., 3N, 6N), at a temperature from about 80° C. to about 118° C. for a period of 30 minutes to 12 hours.

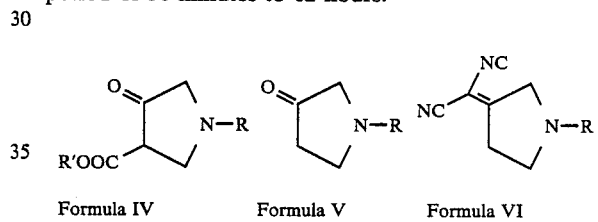

Formula IV     Formula V     Formula VI

Condensation of the pyrrolidine-3-ones of formula V with malonoitrile gives the corresponding dicyanomethylene product of formula VI. The condensation reaction can be performed by treatment of pyrrolidine-3-ones of formula V with malononitrile in a nonpolar solvent such as aromatic hydrocarbon (e.g., benzene or toluene) or ether (e.g., tetrahydrofuran, dioxan, glyme or diglyme) in the presence of a weak inorganic base (such as ammonium, sodium or potassium acetate) or an organic base (such as pyridine, lutidine, colidine, trialkylamine, N,N-dimethylaminoethanol, 4-dimethylaminopyridine, 1,8-diazabicyclo[5,4,0]undex-7-ene or 1,5-diazabicyclo[4,3,0]non-5-ene), at a temperature of from 0° C. to 40° C. for a period of from 30 minutes to 12 hours.

The 3-dicyanomethylenepyrrolidines of formula VI are converted into their corresponding 4-(potential)-formyl derivatives, preferably 4-dimethylaminomethylene derivatives of formula VII in the following manner. Lithiation of the compounds of formula VI with either lithium diisopropylamide or butyl lithium in an etheral solvent such as tetrahydrofuran, dioxan, diethylether, glyme or diglyme, at −78° C. for 12 to 24 hours, followed by treatment with dimethylaminomethylene chloride at a temperature fo from −78° C. to −50° C.

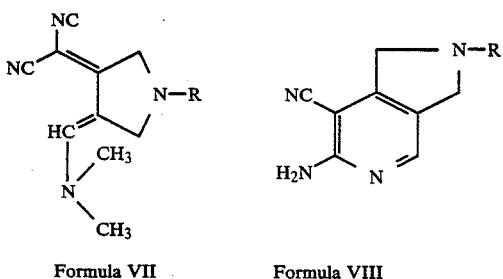

Formula VII          Formula VIII

Upon treatment of compounds of formula VII with aqueous or alcoholic ammonia in a sealed container at a temperature of from 50° C. to 150° C. for a period of from 1 to 8 hours, the corresponding 2,3-dihydropyrrolo[3,4-c]pyridines of formula VIII are obtained.

Condensation of 2,3-dihydropyrrolo[3,4-c]pyridines of formula VIII with N,N-dimethylguanidine in a solvent such as N,N-diethylformamide, N,N-dimethylacetamide, N,N-diethylformamide or a like, at a temperature of from 60° C. to 120° C. for a period of from 12 hours to 2 days affords the corresponding products of formula I.

The second synthetic route for the preparation of the tricyclic system of formula I uses the bicyclic pyrido[2,3-d]pyrimidine derivative, 6-acetoxy-5-methylpyrido[2,3-d]pyrimidine-2,4(1H,3H)-dione compound (IX), as the starting material. Compound IX is converted into the 5-formyl intermediate X by treatment with an oxidizing agent, such as selenium dioxide, manganese dioxide or chromic anhydride, in an organic acid, such as acetic acid, propionic acid and the like, at a temperature of from 25° C. to 107° C. a period for from 3 hours to 48 hours.

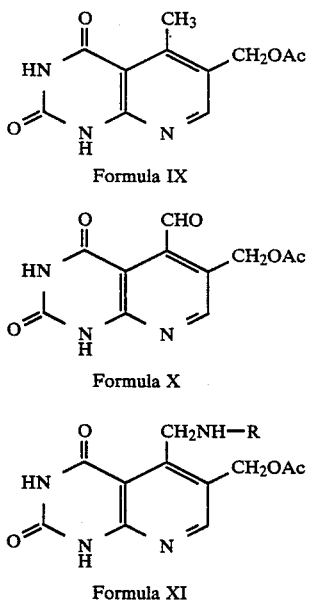

Formula IX

Formula X

Formula XI

Treatment of compounds of formula X with primary amines affords the corresponding Schiff bases, which is then reduced to compounds of formula XI. Schiff bases are prepared in alcohol, such as methanol, ethanol or propanol, or in organic acid, such as acetic acid or propionic acid, or in a mixture of alcohol and organic acid, at temperature of from 20° to 35° C. in a period of from 1 hour to 48 hours.

The reduction of Schiff bases is performed either by catalytic hydrogenation using a metal catalyst, such as palladium on carbon, platinum on carbon, Raney nickel or triphenylphosphine rhodium chloride, in methanol, ethanol or N,N-dimethylformamide, in an hydrogen atmosphere at a pressure range of from 15 psi to 60 psi at room temperature, or by treatment with a reducing agent, such as lithium aluminum hydride, sodium boron hydride, sodium cyanoboron-hydride and the like, in methanol or ethanol.

Intramolecular cyclization of compounds of general formula XI to form compounds of formula I may be carried out by heating to the melting points of respective compounds of formula XI or by heating in an high boiling inert solvent, such as xylene, diglyme or diphenyl ether.

The following Experimental Detail section and Examples are set forth to aid in an understanding of the invention. These sections are not intended to, and should not to be construed to, limit in any way the invention as set forth the claims which follows thereafter.

EXPERIMENTAL DETAIL

Two 6,7-dihydropyrrolo[3,4-c]pyrido[2,3-d]pyrimidines which contain a novel tricyclic ring system of potential bilogical interest were sythesized. 6-(2,5-Dimethoxphenyl)-6,7-dihydropyrrolo[3,4-c]pyrido[2,3-d]pyrido[2,3-d]pyridmidine-2,4(1H,3H)-dione (3a) [throughout the Experimental Detail section, numbers in parenthesis () refer to numbered compounds in FIGS. 1 to 4] was prepared from a pyrido[2,3-d]pyrimidine. 6-Acetoxymethyl-5-methylpyrido[2,3-d]pyrimidine-2,4(1H,3H)-dione (4) was oxidized with $SeO_3$ to the corresponding 5-formyl derivative (5) which was condensed with 2,5-dimethoxyaniline to form the Schiff base. Reduction of the exocyclic azomethine double bond of the Schiff base with $NaBH_3CN$ to (6) followed by thermal cyclization afforded (3a). 2,4-Diamino-6-(4-methoxyphenyl)-6,7-dihydropyrrolo[3,4-c]pyrido[2,3-d]pyrimidine (3b) was synthesized by addition of a pyrimidine ring to the dihydropyrrolo[3,4-c]pyridine system. 1-(4-Methoxphenyl)pyrrolidine-3-one (18) was condensed with malononitrile to give a Knoevenagel adduct (19). Treatment of (19) with N,N-dimethylaminomethylene chloride in the presence of LDA afforded the 4-N,N-dimethylaminomethylenepyrrolidine derivative (20) which was converted into 6-amino-7-cyano-2,3-dihydropyrrolo[3,4-c]pyridine (21) by treatment with $NH_3$/MeOH. Cyclization of (21) with N,N-dimethyl-guanidine afforded the desired product (3b) in high yield.

The chemistry of the pteridine system has been studied extensively since this system is found in the vitamin folic acid (Compound 1, FIG. 1). Folic acid is the essential cofactor in the de novo synthesis of thymidylate and hence DNA. During the biosynthesis of thymidylate folic acid is converted into 5,10-methylenetetrahydrofolic acid (2) which donates one carbon unit to 2'-deoxyuridylic acid. Synthesis of derivatives of the hitherto unknown 6,7-dihydropyrrolo[3,4-c]pyrido[2,3-pyrimidine ring system (Compound 3, FIG. 1) has been attempted (Taylor, E.C., Skotnicki, J.S., Fletcher, S.R. *J. Org. Chem.*, 1985A, 50, 1005; Taylor, E.C., Fletcher, S.R., Fitzjohn, S.L. *J. Org. Chem.*, 1985B, 50, 1010; Gangjee, A., Ohemeng, K.A., *J. Heterocycl. Chem.*, 1984, 21, 873; Gangjee, A., Ohemeng, K.A., Tulachka, J. J. *J. Heterocycl. Chem.*, 1985, 22, 1149; Gangjee, A., Ohemeng, K.A., *J. Heterocycl. Chem.*, 1987, 24, 123) since such derivatives are considered deaza analogues of 2, and may exhibit potent anticancer activity.

Figure 2:
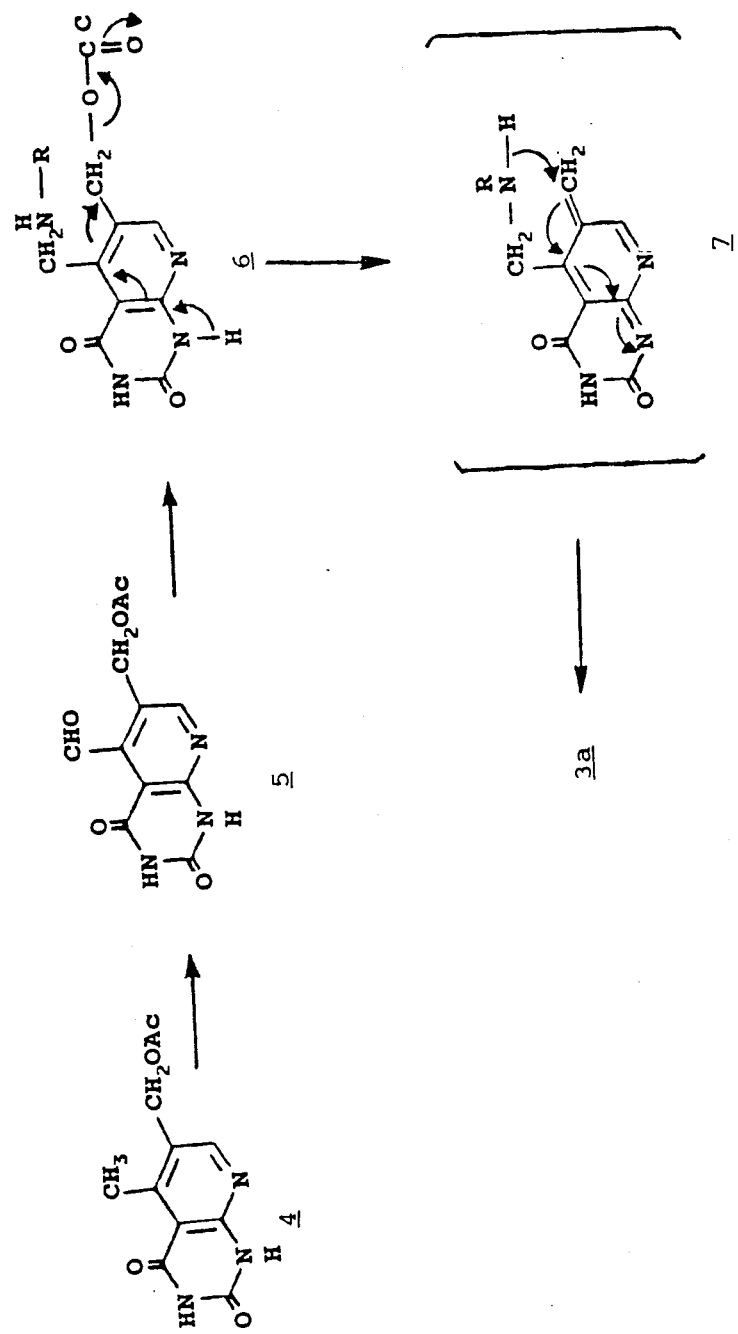
FIG. 2: Synthesis pathway for Compound 3a from 6-acetoxymethyl-5-methylpyrido[2,3-d]pyrimidine-2,4(1H,3H)-dione.
Figure 3:
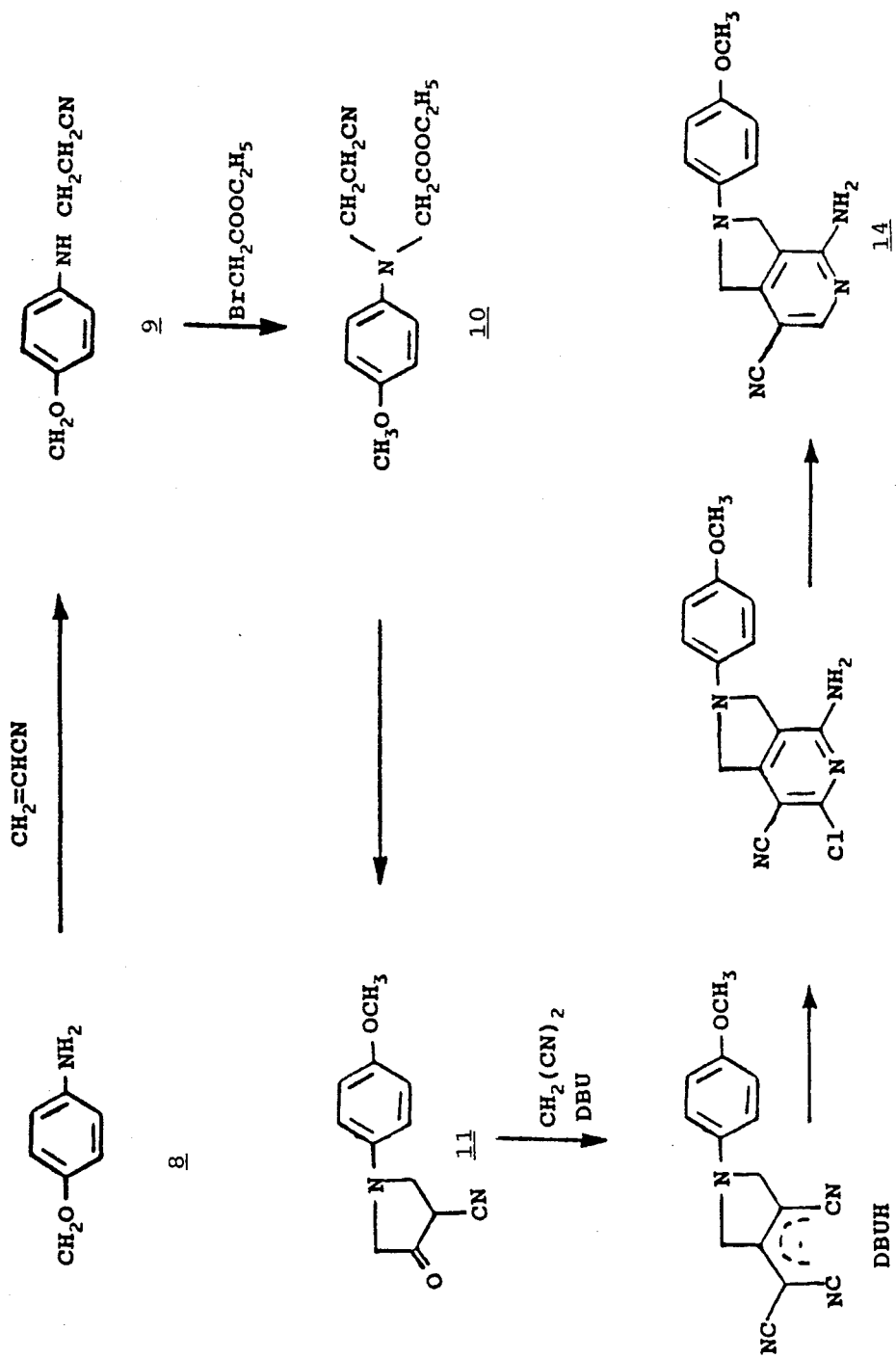
FIG. 3: Synthesis pathway for Compound 14 from p-anisidine (Compound 8).

Recent developements of the preparation of pyrido[2,3-d]pyrimidines from 5-cyano-1,3-dimethyluracil (Su, T-L., Watanabe, K. A., *J. Heterocycl. Chem.*, 1982, 19, 1261, 1984, 21, 1543) prompted the synthesis of (3) from the readily available 6-acetoxymethyl-5-methyl-pyrido[2,3-d]pyrimidin 2,4(1H,3H)-dione (4) (Su, T-L., Huang, J-T., Burchenal, J. H., Watanabe, K. A., Fox, J.J. *J. Med. Chem.*, 1986, 29, 709) by adding the pyrrolidine ring to the bicyclic system. (FIG. 2). This example describes the synthesis of the tricyclic derivative (3a) (X=OH), from the pyrido[2,3-d]pyrimidine intermediates, and also our successful construction of the 2,4-diamino tricyclic compound (3b), X=NH$_2$ from 1-substituted pyrrolidin-3-one (18).

Oxidation of the methyl group of (4) with SeO$_3$ afforded the 5-formyl derivative (5) which was then condensed with 2,5-dimethoxyaniline to form the intermediate Schiff base which was subsequently reduced with sodium cyanoborohydride to yield 5-(2,5-dimethoxyphenyl)aminomethylpyrido[2,3-d]pyrimidine (6). The $^1$H NMR spectrum of (6) showed on singlet at d 0.97 and one broad singlet at d 4.76 corresponding to OCOCH$_3$ and CH$_2$NH, respectively. At 212°-213° C., (6) melted to a clear liquid which resolidified and remelted at 308°-309° C. The $^3$H NMR spectrum of the high melting solid showed the presence of two methylene signals at d 4.67 and 4.98, and the absence of COCH$_3$ signal indicating the tricyclic structure (3) (X=OH). This compound was then prepared in larger amounts by heating (6) in diphenyl ether at 210° C. A posible mechanism for the formation of (3) (X=OH) from (6) is the formation of the methylene intermediate (7). Intramolecular nucleophilic attack by the exocyclic nitrogen on the methylene carbon would lead to the formation of (3) (X=OH) as shown in FIG. 2. Attempts at conversion of (3) (X=OH) into the 2,4-diamino derivative 3 (X=NH$_2$) by the silylation-amination procedure (Su, et al., 1986; Vorbruggen, H., Krolikiewicz, *Chem. Ber.*, 1984, 117, 1523.) failed.

To synthesize the 2,4-diamino analogue (3b) (X=NH$_3$), 4-cyano-1-(4-methoxyphenyl)pyrrolidin-3-one (Compound II, FIG. 3) was used as the starting material which was prepared by the procedure developed for the synthesis of similar pyrrolidin-3-ones. (Southwick, P.L., Madhav, R., Fitzgerald, J.A. *J. Heterocycl Chem.*, 1969, 6, 507). β-(4-Methoxyanilino)-propionitrile (9), obtained by condensation of p-anisidine (8) and acrylonitrile, was alkylated with ethyl bromoacetate to afford N-(β-cyanoethyl)-N-(4-methoxyphenyl)glycinate (10). Compound (10) was subsequently converted into (11) by intramolecular cyclization with a base.

Treatment of (11) with one equivalent each of malononitrile and DBU in benzene afforded the Knoevenagel product, 3-cyano-4-dicyanomethylene-1-(4-methoxyphenyl)pyrrolidine, which was isolated as the crystalline DBU salt (12). The formation of 2,3-dihydropyrrolo[3,4-c]pyridine (13) was achieved by heating (12) at 80° C. for 40 minutes in conc. HCl. The $^3$H NMR spectrum showed the presence of two dissociable protons at d 7.80 in addition to two methylene signals (d 4.29 and 4.53) and an AB quartet intergrated for 4 protons (d 6.54 and 6.86) and an OMe singlet at d 3.68).

Analytical data was consistent with the cyclized structure (13). After reductive dechlorination of (13), the product (14) did not undergo pyrimidine ring formation with guanidine indicating that the amino function was not ortho to the cyano group.

Figure 4:
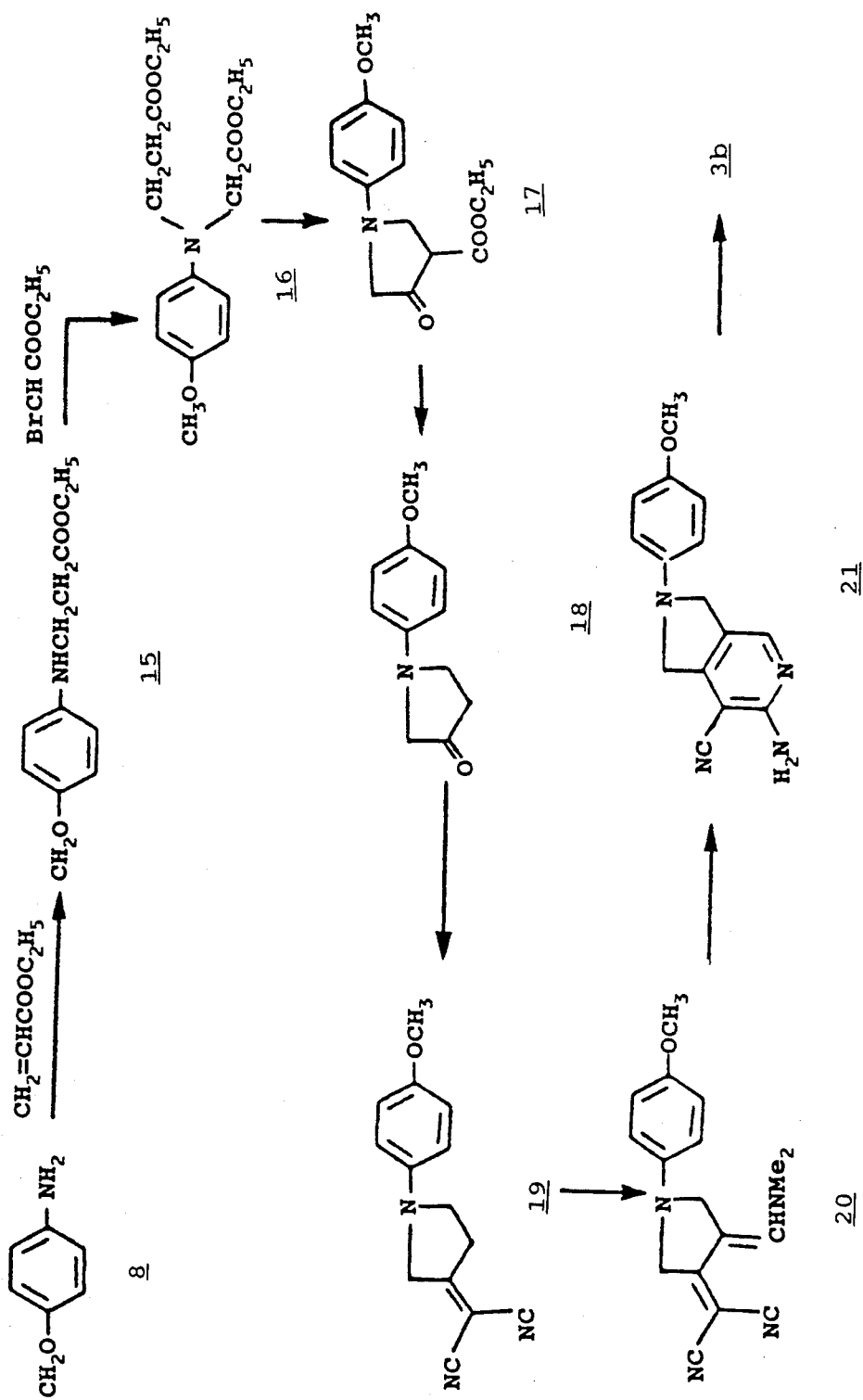
FIG. 4: Synthesis pathway for Compound 3b from p-anisidine (Compound 8).

The 2,4-diamino analogue (3b) (X=NH$_3$) was synthesized from p-anisidine and ethyl acrylate which gave the addition product ethyl (4-methoxphenyl)-β-aminopropionate (Compound 15, FIG. 4). After treatment of (15) with ethyl bromoacetate, the product, ethyl N-(β-ethoxycarbonylethyl)-N-(4-methoxyphenyl) glycinate (16), was converted into 1-(4-methoxyphenyl) (4-ethoxycarbonylpyrrolidin-3-one (17) by an intramolecular Dieckmann reaction. Hydrolysis of ester (17) and decarboxylation of the product to 1-(4-methoxphenyl)pyrrolidine-3-one (18) were performed in situ with 6N HCl (Jaeger, E., J.H., *J. Org. Chem.*, 1965, 30, 740) at 100° C. (bath temperature). The bath had to be removed promptly after evolution of CO$_2$ ceased because (18) was unstable, undergoing decomposition upon prolonged heating. The conditions required for these reactions were rather strict. At higher temperatures, the product decomposed rapidly at lower temperatures, the reactions proceeded much slower, which led to decomposition of (18). Knoevenagel condensation of (18) with malononitrile also required caution since the dicyanomethylene product (19) polymerized readily in solution even at room temperature. Among several reactions attempted to convert (19) into a (potential) 4-formyl intermediate such as (20), the best result was obtained when (19) was lithiated with lithium disopropylamide in THF at −65° C. followed by treatment with dimethylaminomethylene dichloride. (Ege, F., Frey, H. O., Schuck, E. *Synthesis*, 1979, 376). The $^1$H NMR spectrum showed that there were two isolated methylene signals at d 4.23 and 4.44 indicating that the structure of the product was (20). When (20) was treated with NH$_3$/MeOH in a sealed container at 150° C., 6-amino-7-cyano-2,3-dihydropyrrolo[3,4-c]-pyridine (21) was obtained. The $^1$H NMR spectrum of (21) is quite different than that of the isomeric 4-amino congener (14). The methylene protons on C-3 in (14) (d 4.34) are shielded by the peri amino function as compared to those in (21) (d 4.42). The proton on C-6 in (14) (d 8.31), on the other hand, is more deshielded than H-4 in (21) (d 8.21). Condensation of (21) with N,N-dimethylguanidine in DMF at 120° C. (Piper, J. R., McCaleb, G.S., Montgomery, J. A., Kisliuk, R. L., Gaumont, Y., Sirotnak, F.M. *J. Med. Chem.*, 1986, 29, 1080) for 3 days afford the desired 2,4-diamino-N$^6$-(4-methoxyphenyl)-6,7-dihydropyrrolo[3,4-c]pyrido[2,3-d]pyrimidine (3b) in high yield. The $^1$H NMR spectrum showed two singlets at d 4.56 and 4.94 (each integrated for two protons) indicating the presence of two isolated methylene groups in the product.

Although synthesis of the bicyclic 2,3-dihydropyrrolo[3,4-c]pyridine derivatives have been reported, (Godekar, S. M., Frederick, J. L., Semb, J., *J. Am. Chem. Soc.*, 1961, 26, 468; Wright, W. B., Webb, J. S., Smith, J. M. *J. Am. Chem. Soc.*, 1967, 79, 2199; Armarego, W. L. F., Milloy, B. A., Sharma, S. C. *J. Chem. Soc. Perkin I*, 1972, 2485), this invention represents the first synthesis of the tricyclic 6,7-dihydropyrrolo[3,4-c]pyrido[2,3-d]pyrimidine system.

EXAMPLE 1

A mixture of p-anisidine (61.6 g, 0.5 mol) and ethyl acrylate (55.1 g, 0.55 mol) in ethanol (400 mL) is heated under reflux for 3 days. The mixture is concentrated in vacuo, and the residue is fractionally distilled. Ethyl N-(p-methoxphenyl)-b-amino propionate is obtained as colorless liquid (95.6 g, 86%), bp., 155°–159° C. $^1$H NMR (CDCl$_3$) d 1.26 (3H, t, MeCH$_2$), 2.58 (2H, t, b-CH$_2$), 3.39 (2H, t, a-CH$_2$), 3.74 (3H, s, Ome), 4.15 (2H, a, CH$_2$Me), 6.58 and 6.78 (each, 2H, d, Ph).

Microanalyses Calculated for C$_{12}$H$_{17}$NO$_3$: C, 64.55, H, 7.67, N, 6.27%. Found: C, 64,70, H, 7.54, N, 6.22%.

By following the same procedure but using the corresponding amines instead of p-anisidine, the following ethyl N-substituted b-aminopropionates are obtained:
ethyl N-methyl-b-aminopropionate,
ethyl N-ethyl-b-aminopropionate,
ethyl N-(n-propyl)-b-aminopropionate,
ethyl N-(n-butyl)-b-aminopropionate,
ethyl N-cyclopropyl-b-aminopropionate,
ethyl N-cyclopentyl-b-aminopropionate,
ethyl N-cyclohexyl-b-aminopropionate,
ethyl N-cyclohexylmethyl-b-aminopropionate,
ethyl N-phenyl-b-aminopropionate,
ethyl N-(2-methoxyphenyl)-b-aminopropionate,
ethyl N-(3-methoxyphenyl)-b-aminopropionate,
ethyl N-(2,3-dimethoxyphenyl)-b-aminopropionate,
ethyl N-(2,4-dimethoxyphenyl)-b-aminopropionate,
ethyl N-(2,5-dimethoxyphenyl)-b-aminopropionate,
ethyl N-(3,4-dimethoxyphenyl)-b-aminopropionate,
ethyl N-(3,5-dimethoxyphenyl)-b-aminopropionate,
ethyl N-(3,4,5-trimethoxyphenyl)-b-aminopropionate,
ethyl N-(2-methylphenyl)-b-aminopropionate,
ethyl N-(3-methylphenyl)-b-aminopropionate,
ethyl N-(4-methylphenyl)-b-aminopropionate,
ethyl N-(2,3-dimethylphenyl)-b-aminopropionate,
ethyl N-(2,4-dimethylphenyl)-b-aminopropionate,
ethyl N-(2,5-dimethylphenyl)-b-aminopropionate,
ethyl N-(2,6-dimethylphenyl)-b-aminopropionate,
ethyl N-(3,4-dimethylphenyl)-b-aminopropionate,
ethyl N-(3,5-dimethylphenyl)-b-aminopropionate,
ethyl N-(2,4,6-trimethylphenyl)-b-aminopropionate,
ethyl N-(2-fluorophenyl)-b-aminopropionate,
ethyl N-(3-fluorophenyl)-b-aminopropionate,
ethyl N-(4-fluorophenyl)-b-aminopropionate,
ethyl N-(2-chlorophenyl)-b-aminopropionate,
ethyl N-(3-chlorophenyl)-b-aminopropionate,
ethyl N-(4-chlorophenyl)-b-aminopropionate,
ethyl N-(2-bromophenyl)-b-aminopropionate,
ethyl N-(3-bromolphenyl)-b-aminopropionate,
ethyl N-(4-bromophenyl)-b-aminopropionate,
ethyl N-(2,3-difluorophenyl)-b-aminopropionate,
ethyl N-(2,4-difluorophenyl)-b-aminopropionate,
ethyl N-(2,5-difluorophenyl)-b-aminopropionate,
ethyl N-(3,4-difluorophenyl)-b-aminopropionate,
ethyl N-(3,5-difluorophenyl)-b-aminopropionate,
ethyl N-(2,3-dichlorophenyl)-b-aminopropionate,
ethyl N-(2,4-dichlorophenyl)-b-aminopropionate,
ethyl N-(2,5-dichlorophenyl)-b-aminopropionate,
ethyl N-(3,4-dichlorophenyl)-b-aminopropionate,
ethyl N-(3,5-dichlorophenyl)-b-aminopropionate,
ethyl N-(2,3-dibromophenyl)-b-aminopropionate,
ethyl N-(2,4-dibromophenyl)-b-aminopropionate,
ethyl N-(2,5-dibromophenyl)-b-aminopropionate,
ethyl N-(3,4-dibromophenyl)-b-aminopropionate,
ethyl N-(3,5-dibromophenyl)-b-aminopropionate,
ethyl N-(2,4,6-trifluorophenyl)-b-aminopropionate,
ethyl N-(2,4,5-trifluorophenyl)-b-aminopropionate,
ethyl N-(3,4,5-trifluorophenyl)-b-aminopropionate,
ethyl N-(2,4,6-trichlorophenyl)-b-aminopropionate,
ethyl N-(2,4,5-trichlorophenyl)-b-aminopropionate,
ethyl N-(3,4,5-trichlorophenyl)-b-aminopropionate,
ethyl N-(2,4,6-tribromophenyl)-b-aminopropionate,
ethyl N-(2,4,5-tribromophenyl)-b-aminopropionate,
ethyl N-(3,4,5-tribromophenyl)-b-aminopropionate,
ethyl N-benzyl-b-aminopropionate,
ethyl N-(2-methoxybenzyl)-b-aminopropionate,
ethyl N-(3-methoxybenzyl)-b-aminopropionate,
ethyl N-(4-methoxybenzyl)-b-aminopropionate,
ethyl N-(2,4-dimethoxybenzyl)-b-aminopropionate,
ethyl N-(2,5-dimethoxybenzyl)-b-aminopropionate,
ethyl N-(3,4-dimethoxybenzyl)-b-aminopropionate,
ethyl N-(3,5-dimethoxybenzyl)-b-aminopropionate,
ethyl N-(2,4,5-dimethoxybenzyl)-b-aminopropionate,
ethyl N-(3,4,5-dimethoxybenzyl)-b-aminopropionate,
ethyl N-(2-methylbenzyl)-b-aminopropionate,
ethyl N-(3-methylbenzyl)-b-aminopropionate,
ethyl N-(4-methylbenzyl)-b-aminopropionate,
ethyl N-(2,5-dimethylbenzyl)-b-aminopropionate,

EXAMPLE 2

To a stirred mixture of N-(b-ethoxycarbonylethyl)-p-anisidine (178.4 g, 0.8 mol), anhydrous potassium carbonate (150 g, 1.08 mol) in N,N-dimethylformamide (400 mL) is added ethyl bromoacetate (160.5 g, 0.96 mol) over a period of 2 hours at room temperature. The mixture is heated at 60° C. for 10 hours with vigorous stirring, and then poured into ice-cold sodium hydroxide solution (0.1 N, 300 mL). The stirring is continued until the characteristic odor of ethyl bromoacetate disappears. The mixture is extracted with diethyl ether (4×400 mL). The combined extracts were washed with water and then dried over sodium sulfate. After evaporation, the oily residue is purified by fractional distillation to give ethyl N-(b-ethoxycarbonylethyl)-N-(ethoxycarbonylmethyl)glycinate, bp$_a$.d 185°–189° C. (206.2 g, 83%). $^1$H NMR (CDCl$_3$) d 1.24 (6H, t, 2 x MeCH$_2$), 2.63 (2H, t, CH$_2$ CH$_2$N), 3.70 (2H, t, CH$_2$CH$_2$N), 3.73 (3H, s, OMe), 4.04 (2H, s, NCH$_2$CO), 4.12 and 4.16 (each 2H, q, CH$_2$Me), 6.61 and 6.82 (each 2H, d, Ph).

Microanalyses Calculated for C$_{16}$H$_{23}$NO$_5$: C, 62.12, H, 7.49, N, 4.53%. Found: C, 62.38, H, 7.52, N, 4.49%.

By following the same procedure but using the corresponding N-(b-ethoxycarbonylethyl)-p-anisidine, the following ethyl N,N-disubstituted-glycinates are prepared:
N-(b-ethoxycarbonylethyl)-N-methylglycinate,
N-(b-ethoxycarbonylethyl)-N-ethylglycinate,
N-(b-ethoxycarbonylethyl)-N-n-propylglycinate,
N-n-butyl-N-(b-ethoxycarbonyl)glycinate,
N-cyclopropyl-N-(b-ethoxycarbonyl)glycinate,
N-cyclopentyl-N-(b-ethoxycarbonyl)glycinate,
N-cyclohexyl-N-(b-ethoxycarbonylethyl)glycinate,
N-cycolhexylmethyl-N-(b-ethoxycarbonylethyl)glycinate,
N-(b-ethoxycarbonylethyl)-N-phenylglycinate,
N-(b-ethoxycarbonylethyl)-N-(2-methoxyphenyl)glycinate,
N-(b-ethoxycarbonylethyl)-N-(3-methoxyphenyl)glycinate,
N-(2,3-dimethoxyphenyl)-N-(b-ethoxycarbonylethyl)-glycinate,
N-(2,4-dimethoxyphenyl)-N-(b-ethoxycarbonylethyl)-glycinate,
N-(2,5-dimethoxyphenyl)-N-(b-ethoxycarbonylethyl)-glycinate,
N-(3,4-dimethoxyphenyl)-N-(b-ethoxycarbonylethyl)-glycinate, N-(3,5-dimethoxyphenyl)-N-(b-ethoxycarbonylethyl)glycinate,
N-(3,4,5-trimethoxyphenyl)-N-(b-ethoxycarbonylethyl)glycinate,
N-(2-methylphenyl)-N-(b-ethoxycarbonylethyl)glycinate,
N-(3-methylphenyl)-N-(b-ethoxycarbonylethyl)glycinate,
N-(4-methylphenyl)-N-(b-ethoxycarbonylethyl)glycinate,
N-(2,3-dimethylphenyl)-N-(b-ethoxycarbonylethyl)glycinate,
N-(2,4-dimethylphenyl)-N-(b-ethoxycarbonylethyl)glycinate,
N-(2,5-dimethylphenyl)-N-(b-ethoxycarbonylethyl)glycinate,
N-(2,6-dimethylphenyl)-N-(b-ethoxycarbonylethyl)glycinate,
N-(3,4-dimethylphenyl)-N-(b-ethoxycarbonylethyl)glycinate,
N-(3,5-dimethylphenyl)-N-(b-ethoxycarbonylethyl)glycinate,
N-(2,4,6-trimethylphenyl)-N-(b-ethoxycarbonylethyl)glycinate,
N-(b-ethoxycarbonylethyl)-N-(2-fluorophenyl)glycinate,
N-(b-ethoxycarbonylethyl)-N-(3-fluorophenyl)glycinate,
N-(b-ethoxycarbonylethyl)-N-(4-fluorophenyl)glycinate,
N-(b-ethoxycarbonylethyl)-N-(2-chlorophenyl)glycinate,
N-(b-ethoxycarbonylethyl)-N-(3-chlorophenyl)glycinate,
N-(b-ethoxycarbonylethyl)-N-(4-chlorophenyl)glycinate,
N-(b-ethoxycarbonylethyl)-N-(2-bromophenyl)glycinate,
N-(b-ethoxycarbonylethyl)-N-(3-bromophenyl)glycinate,
N-(b-ethoxycarbonylethyl)-N-(4-bromophenyl)glycinate,
N-(2,3-difluorophenyl)-N-(b-ethoxycarbonylethyl)glycinate,
N-(2,4-difluorophenyl)-N-(b-ethoxycarbonylethyl)glycinate,
N-(2,5-difluorophenyl)-N-(b-ethoxycarbonylethyl)glycinate,
N-(3,4-difluorophenyl)-N-(b-ethoxycarbonylethyl)glycinate,
N-(3,5-difluorophenyl)-N-(b-ethoxycarbonylethyl)glycinate,
N-(2,3-dichlorophenyl)-N-(b-ethoxycarbonylethyl)glycinate,
N-(2,4-dichlorophenyl)-N-(b-ethoxycarbonylethyl)glycinate,
N-(2,5-dichlorophenyl)-N-(b-ethoxycarbonylethyl)glycinate,
N-(3,4-dichlorophenyl)-N-(b-ethoxycarbonylethyl)glycinate,
N-(3,5-dichlorophenyl)-N-(b-ethoxycarbonylethyl)glycinate,
N-(2,3-dibromophenyl)-N-(b-ethoxycarbonylethyl)glycinate,
N-(2,4-dibromophenyl)-N-(b-ethoxycarbonylethyl)glycinate,
N-(2,5-dibromophenyl)-N-(b-ethoxycarbonylethyl)glycinate,
N-(3,4-dibromophenyl)-N-(b-ethoxycarbonylethyl)glycinate,
N-(3,5-dibromophenyl)-N-(b-ethoxycarbonylethyl)glycinate,
N-(b-ethoxycarbonylethyl)-N-(2,4,6-trifluorophenyl)glycinate,
N-(b-ethoxycarbonylethyl)-N-(2,4,5-trifluorophenyl)glycinate,
N-(b-ethoxycarbonylethyl)-N-(3,4,5-trifluorophenyl)glycinate,
N-(b-ethoxycarbonylethyl)-N-(2,4,6-trichlorophenyl)glycinate,
N-(b-ethoxycarbonylethyl)-N-(2,4,5-trichlorophenyl)glycinate,
N-(b-ethoxycarbonylethyl)-N-(3,4,5-trichlorophenyl)glycinate,
N-(b-ethoxycarbonylethyl)-N-(2,4,6-tribromophenyl)glycinate,
N-(b-ethoxycarbonylethyl)-N-(2,4,5-tribromophenyl)glycinate,
N-(b-ethoxycarbonylethyl)-N-(3,4,5-tribromophenyl)glycinate,
N-benzyl-N-(b-ethoxycarbonylethyl)glycinate,
N-(b-ethoxycarbonylethyl)-N-(2-methoxybenzyl)glycinate,
N-(b-ethoxycarbonylethyl)-N-(3-methoxybenzyl)glycinate,
N-(b-ethoxycarbonylethyl)-N-(4-methoxybenzyl)glycinate,
N-(2,4-dimethoxybenzyl)-N-(b-ethoxycarbonylethyl)glycinate,
N-(2,5-dimethoxybenzyl)-N-(b-ethoxycarbonylethyl)glycinate,
N-(3,4-dimethoxybenzyl)-N-(b-ethoxycarbonylethyl)glycinate,
N-(3,5-dimethoxybenzyl)-N-(b-ethoxycarbonylethyl)glycinate,
N-(2,4,5-trimethoxybenzyl)-N-(b-ethoxycarbonylethyl)glycinate,
N-(3,4,5-trimethoxybenzyl)-N-(b-ethoxycarbonylethyl)glycinate,
N-(b-ethoxycarbonylethyl)-N-(2-methylbenzyl)glycinate,
N-(b-ethoxycarbonylethyl)-N-(3-methylbenzyl)glycinate,
N-(b-ethoxycarbonylethyl)-N-(4-methylbenzyl)glycinate,
N-(b-ethoxycarbonylethyl)-N-(2,5-dimethylbenzyl)glycinate.

EXAMPLE 3

A solution of ethyl N-(b-ethoxycarbonylethyl)-N-(4-methoxyphenyl)glycinate (106.7 g, 0.345 mol) in dry benzene (400 mL) is added to a mixture of ethanolic sodium ethoxide in benzene (prepared by dissolving 13.1 g of sodium metal in 300 mL of ethanol and then the ethanolic sodium ethoxide solution is diluted with 500 mL of benzene) at room temperature over a period of 90 minutes. The mixture is heated at reflux for 30 minutes and then is cooled to room temperature. The solid is collected by filtration, and then is suspended in an ice-water mixture (1 L). The mixture, after being neutralized with 1 N hydrochloric acid, is extracted with diethyl ether (3×500 mL). The combined extracts are washed with water, dried over sodium sulfate, concentrated, and the residue is crystallized from n-hexane-diethyl ether to afford 1-(4-methoxyphenyl)-4-ethoxycarbonylpyrrolidine-3-one (87.4 g, 64%), mp 58°–60°

C. $^1$H NMR (CDCl$_3$) d 1.34 (3H, dt, CH$_2$Me), 3.76 (3H, s, OMe), 3.75 (2H, dq, CH$_2$Me), 4.14 (2H, s, 2-CH$_2$), 4.12–4.39 (3H, m, H-4 and 5-CH$_2$), 6.46 and 6.86 (each 2H, m, Ph).

Microanalyses Calculated for C$_{12}$H$_{17}$NO$_4$: C, 63.86, H, 6.51, N, 5.32%. Found: C, 63.78, H, 6.56, N, 5.41%.

By following the same procedure but using the corresponding ethyl N,N-disubstituted-glycinates the following 1-substituted 4-ethoxycarbonylpyrrolidine-3-ones are synthesized.

4-ethoxycarbonyl-1-methylpyrrolidine-3-one,
4-ethoxycarbonyl-1-ethylpyrrolidine-3-one,
4-ethoxycarbonyl-1-(n-propyl)pyrrolidine-3-one,
4-ethoxycarbonyl-1-(n-butyl)pyrrolidine-3-one,
4-ethoxycarbonyl-1-cyclopropylpyrrolidine-3-one,
4-ethoxycarbonyl-1-cycopentylpyrrolidine-3-one,
4-ethoxycarbonyl-1-cyclohexylpyrrolidine-3-one,
4-ethoxycarbonyl-1-cyclohexylmethylpyrrolidine-3-one,
4-ethoxycarbonyl-1-phenylpyrrolidine-3-one,
4-ethoxycarbonyl-1-(2-methoxyphenyl)pyrrolidine-3-one,
4-ethoxycarbonyl-1-(3-methoxyphenyl)pyrrolidine-3-one,
4-ethoxycarbonyl-1-(2,3-dimethoxyphenyl)pyrrolidine-3-one,
4-ethoxycarbonyl-1-(2,4-dimethoxyphenyl)pyrrolidine-3-one,
4-ethoxycarbonyl-1-(2,5-dimethoxyphenyl)pyrrolidine-3-one,
4-ethoxycarbonyl-1-(3,4-dimethoxyphenyl)pyrrolidine-3-one,
4-ethoxycarbonyl-1-(3,5-dimethoxyphenyl)pyrrolidine-3-one,
4-ethoxycarbonyl-1-(3,4,5-trimethoxyphenyl)pyrrolidine-3-one,
4-ethoxycarbonyl-1-(2-methylphenyl)pyrrolidine-3-one,
4-ethoxycarbonyl-1-(3-methylphenyl)pyrrolidine-3-one,
4-ethoxycarbonyl-1-(4-methylphenyl)pyrrolidine-3-one,
4-ethoxycarbonyl-1-(2,3-dimethylphenyl)pyrrolidine-3-one,
4-ethoxycarbonyl-1-(2,4-dimethylphenyl)pyrrolidine-3-one,
4-ethoxycarbonyl-1-(2,5-dimethylphenyl)pyrrolidine-3-one,
4-ethoxycarbonyl-1-(3,4-dimethylphenyl)pyrrolidine-3-one,
4-ethoxycarbonyl-1-(3,5-dimethylphenyl)pyrrolidine-3-one,
4-ethoxycarbonyl-1-(3,4,5-trimethylphenyl)pyrrolidine-3-one,
4-ethoxycarbonyl-1-(2-fluorophenyl)pyrrolidine-3-one,
4-ethoxycarbonyl-1-(3-fluorophenyl)pyrrolidine-3-one,
4-ethoxycarbonyl-1-(4-fluorophenyl)pyrrolidine-3-one,
4-ethoxycarbonyl-1-(2-chlorophenyl)pyrrolidine-3-one,
4-ethoxycarbonyl-1-(3-chlorophenyl)pyrrolidine-3-one,
4-ethoxycarbonyl-1-(4-chlorophenyl)pyrrolidine-3-one,
4-ethoxycarbonyl-1-(2-bromophenyl)pyrrolidine-3-one,
4-ethoxycarbonyl-1-(3-bromophenyl)pyrrolidine-3-one,
4-ethoxycarbonyl-1-(4-bromophenyl)pyrrolidine-3-one,
4-ethoxycarbonyl-1-(2,3-difluorophenyl)pyrrolidine-3-one,
4-ethoxycarbonyl-1-(2,4-difluorophenyl)pyrrolidine-3-one,
4-ethoxycarbonyl-1-(2,5-difluorophenyl)pyrrolidine-3-one,
4-ethoxycarbonyl-1-(3,4-difluorophenyl)pyrrolidine-3-one,
4-ethoxycarbonyl-1-(3,5-difluorophenyl)pyrrolidine-3-one,
4-ethoxycarbonyl-1-(2,3-dichlorophenyl)pyrrolidine-3-one,
4-ethoxycarbonyl-1-(2,4-dichlorophenyl)pyrrolidine-3-one,
4-ethoxycarbonyl-1-(2,5-dichlorophenyl)pyrrolidine-3-one,
4-ethoxycarbonyl-1-(3,4-dichlorophenyl)pyrrolidine-3-one,
4-ethoxycarbonyl-1-(3,5-dichlorophenyl)pyrrolidine-3-one,
4-ethoxycarbonyl-1-(2,3-dibromophenyl)pyrrolidine-3-one,
4-ethoxycarbonyl-1-(2,4-dibromophenyl)pyrrolidine-3-one,
4-ethoxycarbonyl-1-(2,5-dibromophenyl)pyrrolidine-3-one,
4-ethoxycarbonyl-1-(3,4-dibromophenyl)pyrrolidine-3-one,
4-ethoxycarbonyl-1-(3,5-dibromophenyl)pyrrolidine-3-one,
4-ethoxycarbonyl-1-(2,4,6-trifluorophenyl)pyrrolidine-3-one,
4-ethoxycarbonyl-1-(2,4,5-trifluorophenyl)pyrrolidine-3-one,
4-ethoxycarbonyl-1-(3,4,5-trifluorophenyl)pyrrolidine-3-one,
4-ethoxycarbonyl-1-(2,4,6-trifluorophenyl)pyrrolidine-3-one,
4-ethoxycarbonyl-1-(3,4,5-trifluorophenyl)pyrrolidine-3-one,
4-ethoxycarbonyl-1-(2,4,6-trichlorophenyl)pyrrolidine-3-one,
4-ethoxycarbonyl-1-(2,4,5-trichlorophenyl)pyrrolidine-3-one,
4-ethoxycarbonyl-1-(3,4,5-trichlorophenyl)pyrrolidine-3-one,
4-ethoxycarbonyl-1-(2,4,6-tribromophenyl)pyrrolidine-3-one,
4-ethoxycarbonyl-1-(2,4,5-tribromophenyl)pyrrolidine-3-one,
4-ethoxycarbonyl-1-(3,4,5-tribromophenyl)pyrrolidine-3-one,
4-ethoxycarbonyl-1-benzylpyrrolidine-3-one,
4-ethoxycarbonyl-1-(2-methoxybenzyl)pyrrolidine-3-one,
4-ethoxycarbonyl-1-(3-methoxybenzyl)pyrrolidine-3-one,
4-ethoxycarbonyl-1-(4-methoxybenzyl)pyrrolidine-3-one,
4-ethoxycarbonyl-1-(2,4-dimethoxybenzyl)pyrrolidine-3-one,
4-ethoxycarbonyl-1-(2,5-dimethoxybenzyl)pyrrolidine-3-one,
4-ethoxycarbonyl-1-(3,4-dimethoxybenzyl)pyrrolidine-3-one,
4-ethoxycarbonyl-1-(3,5-dimethoxybenzyl)pyrrolidine-3-one,
4-ethoxycarbonyl-1-(2,4,5-trimethoxybenzyl)pyrrolidine-3-one,
4-ethoxycarbonyl-1-(3,4,5-trimethoxybenzyl)pyrrolidine-3-one,
4-ethoxycarbonyl-1-(2-methylbenzyl)pyrrolidine-3-one, 4-ethoxycarbonyl-1-(3-methylbenzyl)pyrrolidine-3-one,
4-ethoxycarbonyl-1-(4-methylbenzyl)pyrrolidine-3-one,
4-ethoxycarbonyl-1-(2,5-dimethylbenzyl)pyrrolidine-3-one.

EXAMPLE 4

A mixture of 4-ethoxycarbonyl-1-(4-methoxyphenyl)pyrrolidine-3-one (10.53 g, 0.04 mol) in 6N hydrochloric acid (120 mL) is heated at 100° C. (bath temperature) until evolution of carbon dioxide ceases (about 1 hour). The mixture is cooled in an ice-bath, neutralized with potassium carbonate, and then is extracted with diethyl ether (4×200 mL). The combined extracts are washed with water, dried over sodium sulfate, concentrated, and then the residue is crystallized from diethyl ether-n-hexane to give 1-(4-methoxyphenyl)pyrrolidine-3-one (5.68 g, 67%), mp 104°–105° C. $^1$H NMR (CDCl$_3$) d 2.68 (2H, t, 5-CH$_2$), 3.61 (2H, t, 4-CH$_2$), 3.63 (2H, s, 2-CH$_2$), 3.77 (3H, s, OMe), 6.63 and 6.89 (each 2H, d, Ph).

Microanalyses Calculated for $C_{11}H_{13}NO_2$: C, 69.09, H, 6.85, 7.33%. Found C, 68.95, H, 6.77, N, 7.31%.

By following the same procedure but using the corresponding 4-ethoxycarbonyl-1-substituted-pyrrolidine-3-ones, the following 1-substituted-pyrrolidine-3-ones are prepared:
1-methylpyrrolidine-3-one,
1-ethylpyrrolidine-3-one,
1-(n-propyl)pyrrolidine-3-one,
1-(n-butyl)pyrrolidine-3-one,
1-cyclopropylpyrrolidine-3-one,
1-cyclopentylpyrrolidine-3-one,
1-cyclohexylpyrrolidine-3-one,
1-phenylpyrrolidine-3-one,
1-(2-methoxyphenyl)pyrrolidine-3-one,
1-(3-methoxyphenyl)pyrrolidine-3-one,
1-(2,3-dimethoxyphenyl)pyrrolidine-3-one,
1-(2,4-dimethoxyphenyl)pyrrolidine-3-one,
1-(2,5-dimethoxyphenyl)pyrrolidine-3-one,
1-(3,4-dimethoxyphenyl)pyrrolidine-3-one,
1-(3,5-dimethoxyphenyl)pyrrolidine-3-one,
1-(3,4,5-trimethoxyphenyl)pyrrolidine-3-one,
1-(2-methylphenyl)pyrrolidine-3-one,
1-(3-methylphenyl)pyrrolidine-3-one,
1-(4-methylphenyl)pyrrolidine-3-one,
1-(2,3-dimethylphenyl)pyrrolidine-3-one,
1-(2,4-dimethylphenyl)pyrrolidine-3-one,
1-(2,5-dimethylphenyl)pyrrolidine-3-one,
1-(3,4-dimethylphenyl)pyrrolidine-3-one,
1-(3,5-dimethylphenyl)pyrrolidine-3-one,
1-(2,4,6-trimethylphenyl)pyrrolidine-3-one,
1-(2-fluorophenyl)pyrrolidine-3-one,
1-(3-fluorophenyl)pyrrolidine-3-one,
1-(4-fluorophenyl)pyrrolidine-3-one,
1-(2-chlorophenyl)pyrrolidine-3-one,
1-(3-chlorophenyl)pyrrolidine-3-one,
1-(4-chlorophenyl)pyrrolidine-3-one,
1-(2-bromophenyl)pyrrolidine-3-one,
1-(3-bromophenyl)pyrrolidine-3-one,
1-(4-bromophenyl)pyrrolidine-3-one,
1-(2,3-difluorophenyl)pyrrolidine-3-one,
1-(2,4-difluorophenyl)pyrrolidine-3-one,
1-(2,5-difluorophenyl)pyrrolidine-3-one,
1-(3,4-difluorophenyl)pyrrolidine-3-one,
1-(3,5-difluorophenyl)pyrrolidine-3-one,
1-(2,3-dichlorophenyl)pyrrolidine-3-one,
1-(2,4-dichlorophenyl)pyrrolidine-3-one,
1-(2,5-dichlorophenyl)pyrrolidine-3-one,
1-(3,4-dichlorophenyl)pyrrolidine-3-one,
1-(3,5-dichlorophenyl)pyrrolidine-3-one,
1-(2,3-bromophenyl)pyrrolidine-3-one,
1-(2,4-bromophenyl)pyrrolidine-3-one,
1-(2,5-bromophenyl)pyrrolidine-3-one,
1-(3,4-bromophenyl)pyrrolidine-3-one,
1-(3,5-bromophenyl)pyrrolidine-3-one,
1-(2,4,6-trifluorophenyl)pyrrolidine-3-one,
1-(2,4,5-trifluorophenyl)pyrrolidine-3-one,
1-(3,4,5-trifluorophenyl)pyrrolidine-3-one,
1-(3,4,6-trichlorophenyl)pyrrolidine-3-one,
1-(2,4,5-trichlorophenyl)pyrrolidine-3-one,
1-(3,4,5-trichlorophenyl)pyrrolidine-3-one,
1-(2,4,6-tribromophenyl)pyrrolidine-3-one,
1-(2,4,5-tribromophenyl)pyrrolidine-3-one,
1-(3,4,5-tribromophenyl)pyrrolidine-3-one,
1-benzylpyrrolidine-3-one,
1-(2-methoxybenzyl)pyrrolidine-3-one,
1-(3-methoxybenzyl)pyrrolidine-3-one,
1-(4-methoxybenzyl)pyrrolidine-3-one,
1-(2,4-dimethoxybenzyl)pyrrolidine-3-one,
1-(2,5-dimethoxybenzyl)pyrrolidine-3-one,
1-(3,4-dimethoxybenzyl)pyrrolidine-3-one,
1-(3,5-dimethoxybenzyl)pyrrolidine-3-one,
1-(2,4,5-trimethoxybenzyl)pyrrolidine-3-one,
1-(3,4,5-trimethoxybenzyl)pyrrolidine-3-one,
1-(2-methylbenzyl)pyrrolidine-3-one
1-(3-methylbenzyl)pyrrolidine-3-one
1-(4-methylbenzyl)pyrrolidine-3-one
1-(2,5-dimethylbenzyl)pyrrolidine-3-one

EXAMPLE 5

A mixture of 1-(p-methoxyphenyl)pyrrolidine-3-one (17.41 g, 0.084 mol), malononitrile (6.66 g, 0.1 mol) and 1,5-diazabicyclo[5,4,0]-undec-5-ene (1 mL) in 200 mL of dry benzene is stirred below 10° C. for 2 hours, and then concentrated in vacuo below 20° C. The dark residue is triturated with 200 mL of ethanol to give 3-dicyanomethylene-1-(p-methoxyphenyl)pyrrolidine-3-one (10.5 g, 48%) as a dark green solid, mp 144°–145° C., IR (KBr) 2250 cm$^{-1}$ (CN), $^1$H NMR (CDCl$_3$) d 3.22 (2H, dt, 5-CH$_2$, J=7.0 and 1.4 Hz), 3.56 (2H, dt, 4-CH$_2$, J=7.0 and 1.4 Hz), 3.77 (3H, s, OMe), 4.32 (2H, d, 3-CH$_2$, J=1.4 Hz), 6.64 and 6.69 (each 2H, d, Ph).

Microanalyses Calculated for $C_{14}H_{13}N_3O$: C, 70.27, H, 5.48, N, 17.56%. Found: C, 70.37, H, 5.70, N, 17.69%.

By following the same procedure but using the corresponding 1-substituted pyrrolidines, the following derivatives are synthesized:
3-dicyanomethylene-1-methylpyrrolidine,
3-dicyanomethylene-1-ethylpyrrolidine,
3-dicyanomethylene-1-(n-propyl)pyrrolidine,
3-dicyanomethylene-1-(n-butyl)pyrrolidine,
3-dicyanomethylene-1-cyclopropylpyrrolidine,
3-dicyanomethylene-1-cyclopentylpyrrolidine,
3-dicyanomethylene-1-cyclohexylpyrrolidine,
3-dicyanomethylene-1-cyclohexylmethylpyrrolidine,
3-dicyanomethylene-1-phenylpyrrolidine,
3-dicyanomethylene-1-(2-methoxyphenyl)pyrrolidine,
3-dicyanomethylene-1-(3-methoxyphenyl)pyrrolidine,
3-dicyanomethylene-1-(2,3-dimethoxyphenyl)pyrrolidine,
3-dicyanomethylene-1-(2,4-dimethoxyphenyl)pyrrolidine,
3-dicyanomethylene-1-(2,5-dimethoxyphenyl)pyrrolidine, 3-dicyanomethylene-1-(3,4-dimethoxyphenyl)pyrrolidine,
3-dicyanomethylene-1-(3,5-dimethoxyphenyl)pyrrolidine,
3-dicyanomethylene-1-(3,4,5-trimethoxyphenyl)pyrrolidine,
3-dicyanomethylene-1-(2-methylphenyl)pyrrolidine,
3-dicyanomethylene-1-(3-methylphenyl)pyrrolidine,
3-dicyanomethylene-1-(4-methylphenyl)pyrrolidine,
3-dicyanomethylene-1-(2,3-dimethylphenyl)pyrrolidine,
3-dicyanomethylene-1-(2,4-dimethylphenyl)pyrrolidine,
3-dicyanomethylene-1-(2,5-dimethylphenyl)pyrrolidine,
3-dicyanomethylene-1-(3,4-dimethylphenyl)pyrrolidine,
3-dicyanomethylene-1-(3,5-dimethylphenyl)pyrrolidine,
3-dicyanomethylene-1-(2,4,6-trimethylphenyl)pyrrolidine,
3-dicyanomethylene-1-(2-fluorophenyl)pyrrolidine,
3-dicyanomethylene-1-(3-fluorophenyl)pyrrolidine,
3-dicyanomethylene-1-(4-fluorophenyl)pyrrolidine,
3-dicyanomethylene-1-(2-chlorophenyl)pyrrolidine,
3-dicyanomethylene-1-(3-chlorophenyl)pyrrolidine,
3-dicyanomethylene-1-(4-chlorophenyl)pyrrolidine,
3-dicyanomethylene-1-(2-bromophenyl)pyrrolidine,
3-dicyanomethylene-1-(3-bromophenyl)pyrrolidine,
3-dicyanomethylene-1-(4-bromophenyl)pyrrolidine,
3-dicyanomethylene-1-(2,3-difluorophenyl)pyrrolidine,
3-dicyanomethylene-1-(2,4-difluorophenyl)pyrrolidine,
3-dicyanomethylene-1-(2,5-difluorophenyl)pyrrolidine,
3-dicyanomethylene-1-(3,4-difluorophenyl)pyrrolidine,
3-dicyanomethylene-1-(3,5-difluorophenyl)pyrrolidine,
3-dicyanomethylene-1-(2,3-dichlorophenyl)pyrrolidine
3-dicyanomethylene-1-(2,4-dichlorophenyl)pyrrolidine,
3-dicyanomethylene-1-(2,5-dichlorophenyl)pyrrolidine,
3-dicyanomethylene-1-(3,4-dichlorophenyl)pyrrolidine,
3-dicyanomethylene-1-(3,5-dichlorophenyl)pyrrolidine,
3-dicyanomethylene-1-(2,3-dibromophenyl)pyrrolidine,
3-dicyanomethylene-1-(2,4-dibromophenyl)pyrrolidine,
3-dicyanomethylene-1-(2,5-dibromophenyl)pyrrolidine,
3-dicyanomethylene-1-(3,4-dibromophenyl)pyrrolidine,
3-dicyanomethylene-1-(3,5-dibromophenyl)pyrrolidine,
3-dicyanomethylene-1-(2,4,6-trifluorophenyl)pyrrolidine,
3-dicyanomethylene-1-(2,4,5-trifluorophenyl)pyrrolidine,
3-dicyanomethylene-1-(3,4,5-trifluorophenyl)pyrrolidine,
3-dicyanomethylene-1-(2,4,6-trichlorophenyl)pyrrolidine,
3-dicyanomethylene-1-(2,4,5-trichlorophenyl)pyrrolidine,
3-dicyanomethylene-1-(3,4,5-trichlorophenyl)pyrrolidine,
3-dicyanomethylene-1-(2,4,6-tribromophenyl)pyrrolidine,
3-dicyanomethylene-1-(2,4,5-tribromophenyl)pyrrolidine,
3-dicyanomethylene-1-(3,4,5-tribromophenyl)pyrrolidine,
3-dicyanomethylene-1-benzylpyrrolidine,
3-dicyanomethylene-1-(2-methoxybenzyl)pyrrolidine,
3-dicyanomethylene-1-(3-methoxybenzyl)pyrrolidine,
3-dicyanomethylene-1-(4-methoxybenzyl)pyrrolidine,
3-dicyanomethylene-1-(2,3-dimethoxybenzyl)pyrrolidine,
3-dicyanomethylene-1-(2,4-dimethoxybenzyl)pyrrolidine,
3-dicyanomethylene-1-(2,5-dimethoxybenzyl)pyrrolidine,
3-dicyanomethylene-1-(3,4-dimethoxybenzyl)pyrrolidine,
3-dicyanomethylene-1-(3,5-dimethoxybenzyl)pyrrolidine,
3-dicyanomethylene-1-(2,4,5-trimethoxybenzyl)pyrrolidine,
3-dicyanomethylene-1-(3,4,5-trimethoxybenzyl)pyrrolidine,
3-dicyanomethylene-1-(2-methylbenzyl)pyrrolidine,
3-dicyanomethylene-1-(3-methylbenzyl)pyrrolidine,
3-dicyanomethylene-1-(4-methylbenzyl)pyrrolidine,
3-dicyanomethylene-1-(2,5-dimethylbenzyl)pyrrolidine.

EXAMPLE 6

Lithium diisopropylamide mono(tetrahydrofuran) (7.1 mL, 10.5 mmol, in 1.5M in cyclohexanol) is added dropwise to a suspension of 3-dicyanomethylene-1-(4-methoxyphenyl)pyrrolidine (2.10 g, 8.8 mmol) in 150 mL of freshly distilled (over calcium hydride) tetrahydrofuran in a dry ice-acetone bath. After stirring for 1 hour, dimethylaminomethylene chloride (prepared from 1.64 mL of phosphorus oxychloride and 1.36 mL of N,N-dimethylformamide in 10 mL of tetrahydrofuran) is added dropwise, and the stirring is continued at $-65°$ C. for 18 hours. The solid is collected by filtration and triturated with 50 mL of boiling ethanol to give 3-dicyanomethylene-4-(N,N-dimethylamino)methylene-1-(4-methoxyphenyl)pyrrolidine (1.02 g, 40%), mp 218°–219° C. (decomposition), IR (KBr) 2210 cm$^{-1}$ (CN), $^1$H NMR (Me$_2$SO-d$_6$) d 3.31 (6H, s, NMe$_2$), 3.68 (3H, s, OMe), 4.23 (2H, brs, CH$_2$), 4.44 (2H, brs, CH$_2$), 6.60 and 6.85 (each 2H, d, Ph), 8.24 (1H, s, NCH=).

Microanalyses Calculated for C$_{17}$H$_{18}$N$_4$O. 1/4H$_2$O: C, 68.32, H, 6.24, N, 18.75%. Found: C, 68.41, H, 6.31, N, 18.74%.

By following the same procedure the 1-substituted 3-dicyanomethylenepyrrolidines listed in Example 5, are converted into their corresponding 4-(N,N-dimethylaminomethylene)pyrrolidines.

EXAMPLE 7

A mixture of 3-dicyanomethylene-4-(N,N-dimethylamino)methylene-1-(4-methoxyphenyl)pyrrolidine (2.94 g, 10 mmol) in saturated methanolic ammonia (60 mL) is heated in a sealed steel vessel at 150° C. for 3 hours. After cooling, yellow needles separate are collected by filtration and are washed with methanol to give 6-amino-7-cyano-2,3-dihydro-2-(4-methoxyphenyl)pyrrolo[3,4-c]pyrridine (2.17 g, 81%), mp 242°–243° C. IR (KBr) 2210 cm$^{-1}$ (CN), $^1$H NMR (Me$_2$SO-d$_6$) d 3.68 (3H, s, OMe), 4.42 (2H, brs, 3-CH$_2$), 4.55 (2H, brs, 1-CH$_2$), 6.61 and 6.87 (each 2H, d, Ph), 8.21 (1H, s, H-4).

Microanalyses Calculated for C$_{15}$H$_{14}$N$_4$O: C, 67.65, H, 5.30, N, 21.04%. Found: C, 67.60, H, 5.31, N, 21.13%.

By using the same procedure but using the corresponding 1-substituted 3-dicyanomethylene-4-(N,N-dimethylaminomethylene)-pyrrolidines the following 2-substituted 6-amino-7-cyano-2,3-dihydropyrrolo[3,4-c]pyridines are obtained:

6-amino-7-cyano-2,3-dihydro-2-methylpyrrolo[3,4-c]pyridine,
6-amino-7-cyano-2,3-dihydro-2-ethylpyrrolo[3,4-c]pyridine,
6-amino-7-cyano-2,3-dihydro-2-(n-propyl)pyrrolo[3,4-c]pyridine,
6-amino-7-cyano-2,3-dihydro-2-(n-butyl)pyrrolo[3,4-c]pyridine,
6-amino-7-cyano-2,3-dihydro-2-cyclopentylpyrrolo[3,4-c]pyridine,
6-amino-7-cyano-2,3-dihydro-2-cyclohexylpyrrolo[3,4-c]pyridine,
6-amino-7-cyano-2,3-dihydro-2-cyclohexylmethylpyrrolo[3,4-c]pyridine,
6-amino-7-cyano-2,3-dihydro-2-phenylpyrrolo[3,4-c]pyridine,
6-amino-7-cyano-2,3-dihydro-2-(2-methoxyphenyl)pyrrolo[3,4-c]pyridine,
6-amino-7-cyano-2,3-dihydro-2-(3-methoxyphenyl)pyrrolo[3,4-c]pyridine,
6-amino-7-cyano-2,3-dihydro-2-(2,3-dimethoxyphenyl)pyrrolo[3,4-c]pyridine,
6-amino-7-cyano-2,3-dihydro-2-(2,4-dimethoxyphenyl)pyrrolo[3,4-c]pyridine,
6-amino-7-cyano-2,3-dihydro-2-(2,5-dimethoxyphenyl)pyrrolo[3,4-c]pyridine,
6-amino-7-cyano-2,3-dihydro-2-(3,4-dimethoxyphenyl)pyrrolo[3,4-c]pyridine,
6-amino-7-cyano-2,3-dihydro-2-(3,5-dimethoxyphenyl)pyrrolo[3,4-c]pyridine,
6-amino-7-cyano-2,3-dihydro-2-(3,4,5-trimethoxyphenyl)pyrrolo[3,4-c]pyridine,
6-amino-7-cyano-2,3-dihydro-2-(2-methylphenyl)pyrrolo[3,4-c]pyridine,
6-amino-7-cyano-2,3-dihydro-2-(3-methylphenyl)pyrrolo[3,4-c]pyridine,
6-amino-7-cyano-2,3-dihydro-2-(4-methylphenyl)pyrrolo[3,4-c]pyridine,
6-amino-7-cyano-2,3-dihydro-2-(2,3-dimethylphenyl)pyrrolo[3,4-c]pyridine,
6-amino-7-cyano-2,3-dihydro-2-(2,4-dimethylphenyl)pyrrolo[3,4-c]pyridine,
6-amino-7-cyano-2,3-dihydro-2-(2,5-dimethylphenyl)pyrrolo[3,4-c]pyridine,
6-amino-7-cyano-2,3-dihydro-2-(3,4-dimethylphenyl)pyrrolo[3,4-c]pyridine,
6-amino-7-cyano-2,3-dihydro-2-(3,5-dimethylphenyl)pyrrolo[3,4-c]pyridine,
6-amino-7-cyano-2,3-dihydro-2-(2,4,6-trimethylphenyl)pyrrolo[3,4-c]pyridine,
6-amino-7-cyano-2,3-dihydro-2-(2-fluorophenyl)pyrrolo[3,4-c]pyridine,
6-amino-7-cyano-2,3-dihydro-2-(3-fluorophenyl)pyrrolo[3,4-c]pyridine,
6-amino-7-cyano-2,3-dihydro-2-(4-fluorophenyl)pyrrolo[3,4-c]pyridine,
6-amino-7-cyano-2,3-dihydro-2-(2-chlorophenyl)pyrrolo[3,4-c]pyridine,
6-amino-7-cyano-2,3-dihydro-2-(3-chlorophenyl)pyrrolo[3,4-c]pyridine,
6-amino-7-cyano-2,3-dihydro-2-(4-chlorophenyl)pyrrolo[3,4-c]pyridine,
6-amino-7-cyano-2,3-dihydro-2-(2-bromophenyl)pyrrolo[3,4-c]pyridine,
6-amino-7-cyano-2,3-dihydro-2-(3-bromophenyl)pyrrolo[3,4-c]pyridine,
6-amino-7-cyano-2,3-dihydro-2-(4-bromophenyl)pyrrolo[3,4-c]pyridine,
6-amino-7-cyano-2,3-dihydro-2-(2,3-difluorophenyl)pyrrolo[3,4-c]pyridine,
6-amino-7-cyano-2,3-dihydro-2-(2,4-difluorophenyl)pyrrolo[3,4-c]pyridine,
6-amino-7-cyano-2,3-dihydro-2-(2,5-difluorophenyl)pyrrolo[3,4-c]pyridine,
6-amino-7-cyano-2,3-dihydro-2-(3,4-difluorophenyl)pyrrolo[3,4-c]pyridine,
6-amino-7-cyano-2,3-dihydro-2-(3,5-difluorophenyl)pyrrolo[3,4-c]pyridine,
6-amino-7-cyano-2,3-dihydro-2-(2,3-dichlorophenyl)pyrrolo[3,4-c]pyridine,
6-amino-7-cyano-2,3-dihydro-2-(2,4-dichlorophenyl)pyrrolo[3,4-c]pyridine,
6-amino-7-cyano-2,3-dihydro-2-(2,5-dichlorophenyl)pyrrolo[3,4-c]pyridine,
6-amino-7-cyano-2,3-dihydro-2-(3,4-dichlorophenyl)pyrrolo[3,4-c]pyridine,
6-amino-7-cyano-2,3-dihydro-2-(3,5-dichlorophenyl)pyrrolo[3,4-c]pyridine,
6-amino-7-cyano-2,3-dihydro-2-(2,3-dibromophenyl)pyrrolo[3,4-c]pyridine,
6-amino-7-cyano-2,3-dihydro-2-(2,4-dibromophenyl)pyrrolo[3,4-c]pyridine,
6-amino-7-cyano-2,3-dihydro-2-(2,5-dibromophenyl)pyrrolo[3,4-c]pyridine,
6-amino-7-cyano-2,3-dihydro-2-(3,4-dibromophenyl)pyrrolo[3,4-c]pyridine,
6-amino-7-cyano-2,3-dihydro-2-(3,5-dibromophenyl)pyrrolo[3,4-c]pyridine,
6-amino-7-cyano-2,3-dihydro-2-(2,4,6-trifluorophenyl)pyrrolo[3,4-c]pyridine,
6-amino-7-cyano-2,3-dihydro-2-(2,4,5-trifluorophenyl)pyrrolo[3,4-c]pyridine,
6-amino-7-cyano-2,3-dihydro-2-(3,4,5-trifluorophenyl)pyrrolo[3,4-c]pyridine,
6-amino-7-cyano-2,3-dihydro-2-(2,4,6-trichlorophenyl)pyrrolo[3,4-c]pyridine,
6-amino-7-cyano-2,3-dihydro-2-(2,4,5-trichlorophenyl)pyrrolo[3,4-c]pyridine,
6-amino-7-cyano-2,3-dihydro-2-(3,4,5-trichlorophenyl)pyrrolo[3,4-c]pyridine,
6-amino-7-cyano-2,3-dihydro-2-(2,4,6-tribromophenyl)pyrrolo[3,4-c]pyridine,
6-amino-7-cyano-2,3-dihydro-2-(2,4,5-tribromophenyl)pyrrolo[3,4-c]pyridine,
6-amino-7-cyano-2,3-dihydro-2-(3,4,5-tribromophenyl)pyrrolo[3,4-c]pyridine,
6-amino-7-cyano-2,3-dihydro-2-benzylpyrrolo[3,4-c]pyridine,
6-amino-7-cyano-2,3-dihydro-2-(2-methoxybenzyl)pyrrolo[3,4-c]pyridine,
6-amino-7-cyano-2,3-dihydro-2-(3-methoxybenzyl)pyrrolo[3,4-c]pyridine,
6-amino-7-cyano-2,3-dihydro-2-(4-methoxybenzyl)pyrrolo[3,4-c]pyridine,
6-amino-7-cyano-2,3-dihydro-2-(2,3-dimethoxybenzyl)pyrrolo[3,4-c]pyridine,
6-amino-7-cyano-2,3-dihydro-2-(2,4-dimethoxybenzyl)pyrrolo[3,4-c]pyridine,
6-amino-7-cyano-2,3-dihydro-2-(2,5-dimethoxybenzyl)pyrrolo[3,4-c]pyridine,
6-amino-7-cyano-2,3-dihydro-2-(3,4-dimethoxybenzyl)pyrrolo[3,4-c]pyridine,
6-amino-7-cyano-2,3-dihydro-2-(3,5-dimethoxybenzyl)pyrrolo[3,4-c]pyridine,
6-amino-7-cyano-2,3-dihydro-2-(2,4,5-trimethoxybenzyl)pyrrolo[3,4-c]pyridine, 6-amino-7-cyano-2,3-dihydro-2-(3,4,5-trimethoxybenzyl)pyrrolo[3,4-c]pyridine,
6-amino-7-cyano-2,3-dihydro-2-(2-methylbenzyl)pyrrolo[3,4-c]pyridine,
6-amino-7-cyano-2,3-dihydro-2-(3-methylbenzyl)pyrrolo[3,4-c]pyridine,
6-amino-7-cyano-2,3-dihydro-2-(4-methylbenzyl)pyrrolo[3,4-c]pyridine,
6-amino-7-cyano-2,3-dihydro-2-(2,5-dimethylbenzyl)-pyrrolo[3,4-c]pyridine.

EXAMPLE 8

To solution of potassium tert.-butoxide (94 mg, 0.84 mmol) in N,N-dimethylformamide (8 mL) is added N,N-dimethylguanidine sulfate (204 mg, 0.75 mmol) with stirring. After 15 minutes, 6-amino-7-cyano-2,3-dihydro-2-(4-methoxyphenyl)pyrrolo[3,4-c]pyridine (133 mg, 0.5 mmol) is added. The mixture is heated at 120° C. (bath temperature) under nitrogen atmosphere for 3 days, and then is cooled to room temperature. The yellow solid is collected by filtration, washed with a small volume of N,N-dimethylformamide, and then triturated with boiling water to give 2,4-diamino-6,7-dihydro-6-(4-methoxyphenyl)-pyrrolo[3,4-c]pyrido[2,3-d]pyrimidine (126 mg, 82%), mp 327°–328° C. $^1$H NMR (Me$_2$SO-d$_6$) 3.70 (3H, s, OMe), 4.56 (2H, brs, CH$_2$), 4.94 (2H, brs, CH$_2$), 6.71 (2H, brs, NH$_2$, exchangeable), 6.81 and 6.86 (each 2H, d, Ph), 8.65 (1H, s, H-8).
Microanalyses Calculated for C$_{16}$H$_{16}$N$_6$O·$\frac{1}{4}$H$_2$O: C, 61.43, H, 5.32, N, 26.84%.

By following the same procedure but using the corresponding 2-substituted 6-amino-7-cyano-2,3-dihydropyrrolo[3,4-c]pyridines, the following tricyclic derivatives are synthesized:
2,6-diamino-6,7-dihydro-6-methylpyrrolo[3,4-c]pyrido[2,3-d]pyrimidine,
2,6-diamino-6,7-dihydro-6-ethylpyrrolo[3,4-c]pyrido[2,3-d]pyrimidine,
2,6-diamino-6,7-dihydro-6-(n-propyl)pyrrolo[3,4-c]pyrido[2,3-d]pyrimidine,
2,6-diamino-6,7-dihydro-6-(n-butyl)pyrrolo[3,4-c]pyrido[2,3-d]pyrimidine,
2,6-diamino-6,7-dihydro-6-cyclopropylpyrrolo[3,4-c]pyrido[2,3-d]pyrimidine,
2,6-diamino-6,7-dihydro-6-cyclopentylpyrrolo[3,4-c]pyrido[2,3-d]pyrimidine,
2,6-diamino-6,7-dihydro-6-cyclohexylpyrrolo[3,4-c]pyrido[2,3-d]pyrimidine,
2,6-diamino-6,7-dihydro-6-cyclohexylmethylpyrrolo[3,4-c]pyrido[2,3-d]pyrimidine,
2,6-diamino-6,7-dihydro-6-phenylpyrrolo[3,4-c]pyrido[2,3-d]pyrimidine,
2,6-diamino-6,7-dihydro-6-(2-methoxyphenyl)pyrrolo[3,4-c]pyrido[2,3-d]pyrimidine,
2,6-diamino-6,7-dihydro-6-(3-methoxyphenyl)pyrrolo[3,4-c]pyrido[2,3-d]pyrimidine,
2,6-diamino-6,7-dihydro-6-(2,3-dimethoxyphenyl)pyrrolo[3,4-c]pyrido[2,3-d]pyrimidine,
2,6-diamino-6,7-dihydro-6-(2,4-dimethoxyphenyl)pyrrolo[3,4-c]pyrido[2,3-d]pyrimidine,
2,6-diamino-6,7-dihydro-6-(2,5-dimethoxyphenyl)pyrrolo[3,4-c]pyrido[2,3-d]pyrimidine,
2,6-diamino-6,7-dihydro-6-(3,4-dimethoxyphenyl)pyrrolo[3,4-c]pyrido[2,3-d]pyrimidine,
2,6-diamino-6,7-dihydro-6-(3,5-dimethoxyphenyl)pyrrolo[3,4-c]pyrido[2,3-d]pyrimidine,
2,6-diamino-6,7-dihydro-6-(3,4,5-trimethoxyphenyl)-pyrrolo[3,4-c]pyrido[2,3-d]pyrimidine,
2,6-diamino-6,7-dihydro-6-(2-methylphenyl)pyrrolo[3,4-c]pyrido[2,3-d]pyrimidine,
2,6-diamino-6,7-dihydro-6-(3-methylphenyl)pyrrolo[3,4-c]pyrido[2,3-d]pyrimidine,
2,6-diamino-6,7-dihydro-6-(4-methylphenyl)pyrrolo[3,4-c]pyrido[2,3-d]pyrimidine,
2,6-diamino-6,7-dihydro-6-(2,3-dimethylphenyl)pyrrolo[3,4-c]pyrido[2,3-d]pyrimidine,
2,6-diamino-6,7-dihydro-6-(2,4-dimethylphenyl)pyrrolo[3,4-c]pyrido[2,3-d]pyrimidine,
2,6-diamino-6,7-dihydro-6-(2,5-dimethylphenyl)pyrrolo[3,4-c]pyrido[2,3-d]pyrimidine,
2,6-diamino-6,7-dihydro-6-(3,4-dimethylphenyl)pyrrolo[3,4-c]pyrido[2,3-d]pyrimidine,
2,6-diamino-6,7-dihydro-6-(3,5-dimethylphenyl)pyrrolo[3,4-c]pyrido[2,3-d]pyrimidine,
2,6-diamino-6,7-dihydro-6-(2,4,6-trimethylphenyl)pyrrolo[3,4-c]pyrido[2,3-d]pyrimidine,
2,6-diamino-6,7-dihydro-6-(2-fluorophenyl)pyrrolo[3,4-c]pyrido[2,3-d]pyrimidine,
2,6-diamino-6,7-dihydro-6-(3-fluorophenyl)pyrrolo[3,4-c]pyrido[2,3-d]pyrimidine,
2,6-diamino-6,7-dihydro-6-(4-fluorophenyl)pyrrolo[3,4-c]pyrido[2,3-d]pyrimidine,
2,6-diamino-6,7-dihydro-6-(2-chlorophenyl)pyrrolo[3,4-c]pyrido[2,3-d]pyrimidine,
2,6-diamino-6,7-dihydro-6-(3-chlorophenyl)pyrrolo[3,4-c]pyrido[2,3-d]pyrimidine,
2,6-diamino-6,7-dihydro-6-(4-chlorophenyl)pyrrolo[3,4-c]pyrido[2,3-d]pyrimidine,
2,6-diamino-6,7-dihydro-6-(2-bromophenyl)pyrrolo[3,4-c]pyrido[2,3-d]pyrimidine,
2,6-diamino-6,7-dihydro-6-(3-bromophenyl)pyrrolo[3,4-c]pyrido[2,3-d]pyrimidine,
2,6-diamino-6,7-dihydro-6-(4-bromophenyl)pyrrolo[3,4-c]pyrido[2,3-d]pyrimidine,
2,6-diamino-6,7-dihydro-6-(2,3-difluorophenyl)pyrrolo[3,4-c]pyrido[2,3-d]pyrimidine,
2,6-diamino-6,7-dihydro-6-(2,4-difluorophenyl)pyrrolo[3,4-c]pyrido[2,3-d]pyrimidine,
2,6-diamino-6,7-dihydro-6-(2,5-difluorophenyl)pyrrolo[3,4-c]pyrido[2,3-d]pyrimidine,
2,6-diamino-6,7-dihydro-6-(3,4-difluorophenyl)pyrrolo[3,4-c]pyrido[2,3-d]pyrimidine,
2,6-diamino-6,7-dihydro-6-(3,5-difluorophenyl)pyrrolo[3,4-c]pyrido[2,3-d]pyrimidine,
2,6-diamino-6,7-dihydro-6-(2,3-dichlorophenyl)pyrrolo[3,4-c]pyrido[2,3-d]pyrimidine,
2,6-diamino-6,7-dihydro-6-(2,4-dichlorophenyl)pyrrolo[3,4-c]pyrido[2,3-d]pyrimidine,
2,6-diamino-6,7-dihydro-6-(2,5-dichlorophenyl)pyrrolo[3,4-c]pyrido[2,3-d]pyrimidine,
2,6-diamino-6,7-dihydro-6-(3,4-dichlorophenyl)pyrrolo[3,4-c]pyrido[2,3-d]pyrimidine,
2,6-diamino-6,7-dihydro-6-(3,5-dichlorophenyl)pyrrolo[3,4-c]pyrido[2,3-d]pyrimidine,
2,6-diamino-6,7-dihydro-6-(2,3-dibromophenyl)pyrrolo[3,4-c]pyrido[2,3-d]pyrimidine,
2,6-diamino-6,7-dihydro-6-(2,4-dibromophenyl)pyrrolo[3,4-c]pyrido[2,3-d]pyrimidine,
2,6-diamino-6,7-dihydro-6-(2,5-dibromophenyl)pyrrolo[3,4-c]pyrido[2,3-d]pyrimidine,
2,6-diamino-6,7-dihydro-6-(3,4-dibromophenyl)pyrrolo[3,4-c]pyrido[2,3-d]pyrimidine,
2,6-diamino-6,7-dihydro-6-(3,5-dibromophenyl)pyrrolo[3,4-c]pyrido[2,3-d]pyrimidine,
2,6-diamino-6,7-dihydro-6-(2,4,6-trifluorophenyl)pyrrolo[3,4-c]pyrido[2,3-d]pyrimidine, 2,6-diamino-6,7-dihydro-6-(2,4,5-trifluorophenyl)pyrrolo[3,4-c]pyrido[2,3-d]pyrimidine,
2,6-diamino-6,7-dihydro-6-(3,4,5-trifluorophenyl)pyrrolo[3,4-c]pyrido[2,3-d]pyrimidine,
2,6-diamino-6,7-dihydro-6-(2,4,6-trichlorophenyl)pyrrolo[3,4-c]pyrido[2,3-d]pyrimidine,
2,6-diamino-6,7-dihydro-6-(2,4,5-trichlorophenyl)pyrrolo[3,4-c]pyrido[2,3-d]pyrimidine,
2,6-diamino-6,7-dihydro-6-(3,4,5-trichlorophenyl)pyrrolo[3,4-c]pyrido[2,3-d]pyrimidine,
2,6-diamino-6,7-dihydro-6-(2,4,6-tribromophenyl)pyrrolo[3,4-c]pyrido[2,3-d]pyrimidine,
2,6-diamino-6,7-dihydro-6-(2,4,5-tribromophenyl)pyrrolo[3,4-c]pyrido[2,3-d]pyrimidine,
2,6-diamino-6,7-dihydro-6-(3,4,5-tribromophenyl)pyrrolo[3,4-c]pyrido[2,3-d]pyrimidine,
2,6-diamino-6,7-dihydro-6-benzylpyrrol[3,4-c]pyrido[2,3-d]pyrimidine,
2,6-diamino-6,7-dihydro-6-(2-methoxybenzyl)pyrrolo[3,4-c]pyrido[2,3-d]pyrimidine,
2,6-diamino-6,7-dihydro-6-(3-methoxybenzyl)pyrrolo[3,4-c]pyrido[2,3-d]pyrimidine,
2,6-diamino-6,7-dihydro-6-(4-methoxybenzyl)pyrrolo[3,4-c]pyrido[2,3-d]pyrimidine,
2,6-diamino-6,7-dihydro-6-(2,3-dimethoxybenzyl)pyrrolo[3,4-c]pyrido[2,3-d]pyrimidine,
2,6-diamino-6,7-dihydro-6-(2,4-dimethoxybenzyl)pyrrolo[3,4-c]pyrido[2,3-d]pyrimidine,
2,6-diamino-6,7-dihydro-6-(2,5-dimethoxybenzyl)pyrrolo[3,4-c]pyrido[2,3-d]pyrimidine,
2,6-diamino-6,7-dihydro-6-(3,4-dimethoxybenzyl)pyrrolo[3,4-c]pyrido[2,3-d]pyrimidine,
2,6-diamino-6,7-dihydro-6-(3,5-dimethoxybenzyl)pyrrolo[3,4-c]pyrido[2,3-d]pyrimidine,
2,6-diamino-6,7-dihydro-6-(2,4,5-trimethoxybenzyl)pyrrolo[3,4-c]pyrido[2,3-d]pyrimidine,
2,6-diamino-6,7-dihydro-6-(3,4,5-trimethoxybenzyl)pyrrolo[3,4-c]pyrido[2,3-d]pyrimidine,
2,6-diamino-6,7-dihydro-6-(2-methylbenzyl)pyrrolo[3,4-c]pyrido[2,3-d]pyrimidine,
2,6-diamino-6,7-dihydro-6-(3-methylbenzyl)pyrrolo[3,4-c]pyrido[2,3-d]pyrimidine,
2,6-diamino-6,7-dihydro-6-(4-methylbenzyl)pyrrolo[3,4-c]pyrido[2,3-d]pyrimidine,
2,6-diamino-6,7-dihydro-6-(2,5-dimethylbenzyl)pyrrolo[3,4-c]pyrido[2,3-d]pyrimidine.

EXAMPLE 9

A mixture of 6-acetoxymethyl-5-methylpyrido[2,3-d]pyrimidine-2,4(1H,3H)-dione (3.14 g, 12.5 mmol) and selenium dioxide (2.09 g, 18.9 mmol) in glacial acetic acid (100 mL) is heated at reflux for 20 hours, and then the mixture is filtered through a Celite pad while hot. The filtrate is concentrated in vacuo, and the residue is crystallized from methanol to give 6-acetoxymethyl-5-formylpyrido[2,3-d]-pyrimidine-2,4(1H, 3H)-dione (2.94 g, 86.6%), mp 263°–264° C. (decomposition). $^1$H NMR (Me$_2$SO-d$_6$) d 2.02 (3H, s, Ac), 5.03 (2H, s, CH$_2$), 8.75 (1H, s, H-7), 10.49 (1H, s, CHO).

Microanalyses Calculated for C$_{11}$H$_9$N$_3$O$_5$: C, 50.19, H, 3.45, N, 15.97%. Found: C, 49.94, H, 3.57, N, 15.80%.

EXAMPLE 10

A mixture of 6-acetoxymethyl-5-formylpyrido[2,3-d]pyrimidine-2,4-(1H,3H)-dione (526.4 mg, 2 mmol) and 2,5-dimethoxyaniline (398.3 mg, 2.6 mmol) in glacial acetic acid (20 mL) is stirred at room temperature for 5 hours under nitrogen. The mixture is concentrated in vacuo. Traces of acetic acid are removed azeotropically by several co-evaporations with ethanol, and the residue is suspended in absolute ethanol (80 mL). To the suspension is added sodium cyanoborohydride (251 mg, 4 mmol), and the mixture is stirred for 4 hours at room temperature. The solid which is collected by filtration is dissolved in a mixture of chloroform and methanol (20 mL, 1:1 v/v), and the solution is absorbed on 5 grams of silica gel, which is placed on the top of a silica gel column (3×40 cm). The column is washed with chloroform containing 0.5% (by volume) of methanol to elute the product, 6-acetoxymethyl-5-(2,5-dimethoxyanilino)methylpyrido[2,3-d]-pyrimidine-2,4(1H,3H)dione (616 mg, 77%) which melts at 212°–213° C., resolidifies and remelts at 308°–310° C. $^1$H NMR (Me$_2$SO-d$_6$) d 0.97 (3H, s, Ac), 3.64 (3H, s, OMe), 3.65 (3H, s, OMe), 4.76 (2H, brs, CH$_2$NH), 5.14 (1H, brs, CH$_2$NH), 5.23 (2H, s, CH$_2$O), 6.10 (1H, dd, H-4', J$_{3',4'}$=8.5, J$_{4',6'}$=2.7 Hz), 6.34 (1H, d, H-3', J$_{3',4'}$=8.5 Hz), 6.68 (1H, d, H-6', J$_{4',6'}$=2.7 Hz), 8.57 (1H, s, H-7), 11.48 (1H, brs, NH, exchangeable), 11.72 (1H, brs, NH, exchangeable).

Microanalyses Calculated for C$_{19}$H$_{20}$N$_4$O$_6$: C, 57.00, H, 5.03, N, 13.99%. Found: C, 56.97, H, 5.07, N, 14.10.

By following the same procedure but using the corresponding amines, the following compounds are obtained:

6-acetoxymethyl-5-methylaminomethylpyrido[2,3-d]pyrimidine-2,4(1H,3H)-dione,
6-acetoxymethyl-5-ethylaminomethylpyrido[2,3-d]pyrimidine-2,4(1H,3H)-dione,
6-acetoxymethyl-5-(n-propyl)aminomethylpyrido[2,3-d]pyrimidine-2,4(1H,3H)-dione,
6-acetoxymethyl-5-(n-butyl)aminomethylpyrido[2,3-d]pyrimidine-2,4(1H,3H)-dione,
6-acetoxymethyl-5-cyclopropylaminomethylpyrido[2,3-d]pyrimidine-2,4(1H,3H)-dione,
6-acetoxymethyl-5-cyclopentylaminomethylpyrido[2,3-d]pyrimidine-2,4(1H,3H)-dione,
6-acetoxymethyl-5-cyclohexylaminomethylpyrido[2,3-d]pyrimidine-2,4(1H,3H)-dione,
6-acetoxymethyl-5-cyclohexymethylaminomethylpyrido[2,3-d]pyrimidine-2,4(1H,3H)-dione,
6-acetoxymethyl-5-anilinomethylpyrido[2,3-d]pyrimidine-2,4(1H,3H)-dione,
6-acetoxymethyl-5-(2-methoxyanilino)methylpyrido[2,3-d]pyrimidine-2,4(1H,3H)-dione,
6-acetoxymethyl-5-(3-methoxyanilino)methylpyrido[2,3-d]pyrimidine-2,4(1H,3H)-dione,
6-acetoxymethyl-5-(4-methoxyanilino)methylpyrido[2,3-d]pyrimidine-2,4(1H,3H)-dione,
6-acetoxymethyl-5-(2,3-dimethoxyanilino)methylpyrido[2,3-d]pyrimidine-2,4(1H,3H)-dione,
6-acetoxymethyl-5-(2,4-dimethoxyanilino)methylpyrido[2,3-d]pyrimidine-2,4(1H,3H)-dione,
6-acetoxymethyl-5-(3,4-dimethoxyanilino)methylpyrido[2,3-d]pyrimidine-2,4(1H,3H)-dione,
6-acetoxymethyl-5-(3,5-dimethoxyanilino)methylpyrido[2,3-d]pyrimidine-2,4(1H,3H)-dione,
6-acetoxymethyl-5-(3,4,5-dimethoxyanilino)methylpyrido[2,3-d]pyrimidine-2,4(1H,3H)-dione,
6-acetoxymethyl-5-(2-methylanilino)methylpyrido[2,3-d]pyrimidine-2,4(1H,3H)-dione,
6-acetoxymethyl-5-(3-methylanilino)methylpyrido[2,3-d]pyrimidine-2,4(1H,3H)-dione,
6-acetoxymethyl-5-(4-methylanilino)methylpyrido[2,3-d]pyrimidine-2,4(1H,3H)-dione, 6-acetoxymethyl-5-(2,3-dimethylanilino)methyl-pyrido[2,3-d]pyrimidine-2,4(1H,3H)-dione,
6-acetoxymethyl-5-(2,4-dimethylanilino)methyl-pyrido[2,3-d]pyrimidine-2,4(1H,3H)-dione,
6-acetoxymethyl-5-(2,5-dimethypanilino)methyl-pyrido[2,3-d]pyrimidine-2,4(1H,3H)-dione,
6-acetoxymethyl-5-(3,4-dimethypanilino)methyl-pyrido[2,3-d]pyrimidine-2,4(1H,3H)-dione,
6-acetoxymethyl-5-(3,5-dimethypanilino)methyl-pyrido[2,3-d]pyrimidine-2,4(1H,3H)-dione,
6-acetoxymethyl-5-(2,4,6-trimethylanilino)methyl-pyrido[2,3-d]pyrimidine-2,4(1H,3H)-dione,
6-acetoxymethyl-5-(2-fluoroanilino)methylpyrido[2,3-d]pyrimidine-2,4(1H,3H)-dione,
6-acetoxymethyl-5-(3-fluoroanilino)methylpyrido[2,3-d]pyrimidine-2,4(1H,3H)-dione,
6-acetoxymethyl-5-(4-fluoroanilino)methylpyrido[2,3-d]pyrimidine-2,4(1H,3H)-dione,
6-acetoxymethyl-5-(2-chloroanilino)methylpyrido[2,3-d]pyrimidine-2,4(1H,3H)-dione,
6-acetoxymethyl-5-(3-chloroanilino)methylpyrido[2,3-d]pyrimidine-2,4(1H,3H)-dione,
6-acetoxymethyl-5-(4-chloroanilino)methylpyrido[2,3-d]pyrimidine-2,4(1H,3H)-dione,
6-acetoxymethyl-5-(2,3-difluoroanilino)methyl-pyrido[2,3-d]pyrimidine-2,4(1H,3H)-dione,
6-acetoxymethyl-5-(2,4-difluoroanilino)methyl-pyrido[2,3-d]pyrimidine-2,4(1H,3H)-dione,
6-acetoxymethyl-5-(2,5-difluoroanilino)methyl-pyrido[2,3-d]pyrimidine-2,4(1H,3H)-dione,
6-acetoxymethyl-5-(3,4-difluoroanilino)methyl-pyrido[2,3-d]pyrimidine-2,4(1H,3H)-dione,
6-acetoxymethyl-5-(3,5-difluoroanilino)methyl-pyrido[2,3-d]pyrimidine-2,4(1H,3H)-dione,
6-acetoxymethyl-5-(2,3-dichloroanilino)methyl-pyrido[2,3-d]pyrimidine-2,4(1H,3H)-dione,
6-acetoxymethyl-5-(2,4-dichloroanilino)methyl-pyrido[2,3-d]pyrimidine-2,4(1H,3H)-dione,
6-acetoxymethyl-5-(2,5-dichloroanilino)methyl-pyrido[2,3-d]pyrimidine-2,4(1H,3H)-dione,
6-acetoxymethyl-5-(3,4-dichloroanilino)methyl-pyrido[2,3-d]pyrimidine-2,4(1H,3H)-dione,
6-acetoxymethyl-5-(3,5-dichloroanilino)methyl-pyrido[2,3-d]pyrimidine-2,4(1H,3H)-dione,
6-acetoxymethyl-5-(benzylaminomethylpyrido[2,3-d]pyrimidine-2,4(1H,3H)-dione,
6-acetoxymethyl-5-(2-methoxybenzylamino)methyl-pyrido[2,3-d]pyrimidine-2,4(1H,3H)-dione,
6-acetoxymethyl-5-(3-methoxybenzylamino)methyl-pyrido[2,3-d]pyrimidine-2,4(1H,3H)-dione,
6-acetoxymethyl-5-(4-methoxybenzylamino)methyl-pyrido[2,3-d]pyrimidine-2,4(1H,3H)-dione,
6-acetoxymethyl-5-(2,3-dimethoxybenzylamino)methylpyrido[2,3-d]pyrimidine-2,4(1H,3H)-dione,
6-acetoxymethyl-5-(2,4-dimethoxybenzylamino)methylpyrido[2,3-d]pyrimidine-2,4(1H,3H)-dione,
6-acetoxymethyl-5-(2,5-dimethoxybenzylamino)methylpyrido[2,3-d]pyrimidine-2,4(1H,3H)-dione,
6-acetoxymethyl-5-(3,4-dimethoxybenzylamino)methylpyrido[2,3-d]pyrimidine-2,4(1H,3H)-dione,
6-acetoxymethyl-5-(3,5-dimethoxybenzylamino)methylpyrido[2,3-d]pyrimidine-2,4(1H,3H)-dione,
6-acetoxymethyl-5-(2,4,5-trimethoxybenzylamino)methylpyrido[2,3-d]pyrimidine-2,4(1H,3H)-dione,
6-acetoxymethyl-5-(3,4,5-trimethoxybenzylamino)methylpyrido[2,3-d]pyrimidine-2,4(1H,3H)-dione,
6-acetoxymethyl-5-(2-methylbenzylamino)methyl-pyrido[2,3-d]pyrimidine-2,4(1H,3H)-dione,
6-acetoxymethyl-5-(3-methylbenzylamino)methyl-pyrido[2,3-d]pyrimidine-2,4(1H,3H)-dione,
6-acetoxymethyl-5-(4-methylbenzylamino)methyl-pyrido[2,3-d]pyrimidine-2,4(1H,3H)-dione,
6-acetoxymethyl-5-(2,5-dimethylbenzylamino)methyl-pyrido[2,3-d]pyrimidine-2,4(1H,3H)-dione.

EXAMPLE 11

6-Acetoxymethyl-5-(2,5-dimethoxyanilino)methyl-pyrido[2,3-d]-pyrimidine-2,4(1H,3H)-dione (400 mg, 1 mmol) in diphenyl ether is heated at 210° C. for 2 hours under nitrogen. The resulting clear solution is cooled and then is diluted with a 1:1 mixture of ethanol and diethyl ether (100 mL). The yellow precipitate is collected by filtration and is washed with boiling mixture of chloroform and ethanol (1:1 v/v) to give 6-(2,5-dimethoxyphenyl)-6,7-dihydropyrrolo[3,4-d]pyrimidine-2,4(1H,3H)-dione (311 mg, 91%), mp 308°-310° C. $^1$H NMR (Me$_2$SO-d$_6$) d 3.70 (3H, s, OMe), 3.74 (3H, s, OMe), 4.67 (2H, brs, CH$_2$), 4.98 (2H, brs, CH$_2$), 6.28 (1H, s, H-6'), 6.31 and 6.87 (each 1H, d, H-3' and H-4'), 8.53 (1H, s, H-2), 11.43 and 11.61 (each 1H, brs, NH, exchangeable).

By following the same procedure but using the corresponding 5-substituted 6-acetoxymethylpyrido[2,3-d]pyrimidine-2,4(1H,3H)-dione, the following tricyclic compounds are synthesized:
6-methyl-6,7-dihydropyrrolo[3,4-c]pyrido[2,3-d]pyrimidine-2,4(1H,3H)-dione,
6-ethyl-6,7-dihydropyrrolo[3,4-c]pyrido[2,3-d]pyrimidine-2,4(1H,3H)-dione,
6-(n-propyl)-6,7-dihydropyrrolo[3,4-c]pyrido[2,3-d]pyrimidine-2,4(1H,3H)-dione,
6-(n-butyl)-6,7-dihydropyrrolo[3,4-c]pyrido[2,3-d]pyrimidine-2,4(1H,3H)-dione,
6-cyclopropyl-6,7-dihydropyrrolo[3,4-c]pyrido[2,3-d]pyrimidine-2,4(1H,3H)-dione,
6-cyclopentyl-6,7-dihydropyrrolo[3,4-c]pyrido[2,3-d]pyrimidine-2,4(1H,3H)-dione,
6-cyclohexyl-6,7-dihydropyrrolo[3,4-c]pyrido[2,3-d]pyrimidine-2,4(1H,3H)-dione,
6-cyclohexylmethyl-6,7-dihydropyrrolo[3,4-c]pyrido[2,3-d]pyrimidine-2,4(1H,3H)-dione,
6-phenyl-6,7-dihydropyrrolo[3,4-c]pyrido[2,3-d]pyrimidine-2,4(1H,3H)-dione,
6-(2-methoxyphenyl)-6,7-dihydropyrrolo[3,4-c]pyrido[2,3-d]pyrimidine-2,4(1H,3H)-dione,
6-(3-methoxyphenyl)-6,7-dihydropyrrolo[3,4-c]pyrido[2,3-d]pyrimidine-2,4(1H,3H)-dione,
6-(4-methoxyphenyl)-6,7-dihydropyrrolo[3,4-c]pyrido[2,3-d]pyrimidine-2,4(1H,3H)-dione,
6-(2,3-dimethoxyphenyl)-6,7-dihydropyrrolo[3,4-c]pyrido[2,3-d]pyrimidine-2,4(1H,3H)-dione,
6-(2,4-dimethoxyphenyl)-6,7-dihydropyrrolo[3,4-c]pyrido[2,3-d]pyrimidine-2,4(1H,3H)-dione,
6-(3,4-dimethoxyphenyl)-6,7-dihydropyrrolo[3,4-c]pyrido[2,3-d]pyrimidine-2,4(1H,3H)-dione,
6-(3,5-dimethoxyphenyl)-6,7-dihydropyrrolo[3,4-c]pyrido[2,3-d]pyrimidine-2,4(1H,3H)-dione,
6-(3,4,5-trimethoxyphenyl)-6,7-dihydropyrrolo[3,4-c]pyrido[2,3-d]pyrimidine-2,4(1H,3H)-dione,
6-(2-methylphenyl)-6,7-dihydropyrrolo[3,4-c]pyrido[2,3-d]pyrimidine-2,4(1H,3H)-dione,
6-(3-methylphenyl)-6,7-dihydropyrrolo[3,4-c]pyrido[2,3-d]pyrimidine-2,4(1H,3H)-dione,
6-(4-methylphenyl)-6,7-dihydropyrrolo[3,4-c]pyrido[2,3-d]pyrimidine-2,4(1H,3H)-dione, 6-(2,3-dimethylphenyl)-6,7-dihydropyrrolo[3,4-c]pyrido[2,3-d]pyrimidine-2,4(1H,3H)-dione,
6-(2,4-dimethylphenyl)-6,7-dihydropyrrolo[3,4-c]pyrido[2,3-d]pyrimidine-2,4(1H,3H)-dione,
6-(2,5-dimethylphenyl)-6,7-dihydropyrrolo[3,4-c]pyrido[2,3-d]pyrimidine-2,4(1H,3H)-dione,
6-(3,4-dimethylphenyl)-6,7-dihydropyrrolo[3,4-c]pyrido[2,3-d]pyrimidine-2,4(1H,3H)-dione,
6-(3,5-dimethylphenyl)-6,7-dihydropyrrolo[3,4-c]pyrido[2,3-d]pyrimidine-2,4(1H,3H)-dione,
6-(2,4,6-trimethylphenyl)-6,7-dihydropyrrolo[3,4-c]pyrido[2,3-d]pyrimidine-2,4(1H,3H)-dione,
6-(2-fluorophenyl)-6,7-dihydropyrrolo[3,4-c]pyrido[2,3-d]pyrimidine-2,4(1H,3H)-dione,
6-(3-fluorophenyl)-6,7-dihydropyrrolo[3,4-c]pyrido[2,3-d]pyrimidine-2,4(1H,3H)-dione,
6-(4-fluorophenyl)-6,7-dihydropyrrolo[3,4-c]pyrido[2,3-d]pyrimidine-2,4(1H,3H)-dione,
6-(2-chlorophenyl)-6,7-dihydropyrrolo[3,4-c]pyrido[2,3-d]pyrimidine-2,4(1H,3H)-dione,
6-(3-chlorophenyl)-6,7-dihydropyrrolo[3,4-c]pyrido[2,3-d]pyrimidine-2,4(1H,3H)-dione,
6-(4-chlorophenyl)-6,7-dihydropyrrolo[3,4-c]pyrido[2,3-d]pyrimidine-2,4(1H,3H)-dione,
6-(2,3-difluorophenyl)-6,7-dihydropyrrolo[3,4-c]pyrido[2,3-d]pyrimidine-2,4(1H,3H)-dione,
6-(2,4-difluorophenyl)-6,7-dihydropyrrolo[3,4-c]pyrido[2,3-d]pyrimidine-2,4(1H,3H)-dione,
6-(2,5-difluorophenyl)-6,7-dihydropyrrolo[3,4-c]pyrido[2,3-d]pyrimidine-2,4(1H,3H)-dione,
6-(3,4-difluorophenyl)-6,7-dihydropyrrolo[3,4-c]pyrido[2,3-d]pyrimidine-2,4(1H,3H)-dione,
6-(3,5-difluorophenyl)-6,7-dihydropyrrolo[3,4-c]pyrido[2,3-d]pyrimidine-2,4(1H,3H)-dione,
6-(2,3-dichlorophenyl)-6,7-dihydropyrrolo[3,4-c]pyrido[2,3-d]pyrimidine-2,4(1H,3H)-dione,
6-(2,4-dichlorophenyl)-6,7-dihydropyrrolo[3,4-c]pyrido[2,3-d]pyrimidine-2,4(1H,3H)-dione,
6-(2,5-dichlorophenyl)-6,7-dihydropyrrolo[3,4-c]pyrido[2,3-d]pyrimidine-2,4(1H,3H)-dione,
6-(3,4-dichlorophenyl)-6,7-dihydropyrrolo[3,4-c]pyrido[2,3-d]pyrimidine-2,4(1H,3H)-dione,
6-(3,5-dichlorophenyl)-6,7-dihydropyrrolo[3,4-c]pyrido[2,3-d]pyrimidine-2,4(1H,3H)-dione,
6-benzyl-6,7-dihydropyrrolo[3,4-c]pyrido[2,3-d]pyrimidine-2,4(1H,3H)-dione,
6-(2-methoxybenzyl)-6,7-dihydropyrrolo[3,4-c]pyrido[2,3-d]pyrimidine-2,4(1H,3H)-dione,
6-(3-methoxybenzyl)-6,7-dihydropyrrolo[3,4-c]pyrido[2,3-d]pyrimidine-2,4(1H,3H)-dione,
6-(4-methoxybenzyl)-6,7-dihydropyrrolo[3,4-c]pyrido[2,3-d]pyrimidine-2,4(1H,3H)-dione,
6-(2,3-dimethoxybenzyl)-6,7-dihydropyrrolo[3,4-c]pyrido[2,3-d]pyrimidine-2,4(1H,3H)-dione,
6-(2,4-dimethoxybenzyl)-6,7-dihydropyrrolo[3,4-c]pyrido[2,3-d]pyrimidine-2,4(1H,3H)-dione,
6-(2,5-dimethoxybenzyl)-6,7-dihydropyrrolo[3,4-c]pyrido[2,3-d]pyrimidine-2,4(1H,3H)-dione,
6-(3,4-dimethoxybenzyl)-6,7-dihydropyrrolo[3,4-c]pyrido[2,3-d]pyrimidine-2,4(1H,3H)-dione,
6-(3,5-dimethoxybenzyl)-6,7-dihydropyrrolo[3,4-c]pyrido[2,3-d]pyrimidine-2,4(1H,3H)-dione,
6-(2,4,5-dimethoxybenzyl)-6,7-dihydropyrrolo[3,4-c]pyrido[2,3-d]pyrimidine-2,4(1H,3H)-dione,
6-(3,4,5-trimethoxybenzyl)-6,7-dihydropyrrolo[3,4-c]pyrido[2,3-d]pyrimidine-2,4(1H,3H)-dione.

What is claimed is:

1. A compound having the structure:

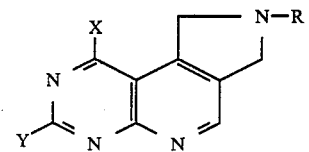

wherein X and Y are the same or different and each is an OH, NH$_2$ or SH group; and wherein R is a lower alkyl group, an aryl group, a substituted aryl group, an alkylaryl group or a substituted alkylaryl group and each substituent of the substituted aryl group or the substituted alkylaryl group is an lower alkyl group, an alkoxy group, or a halogen.

2. A compound of claim 1, wherein the lower alkyl group has 1 to 7 carbon atoms; the substituted aryl group is a mono-, di-, or tri-substituted aryl group; the alkylaryl group is an alkylphenyl or alkylbenzyl group; the substituted alkylaryl group is a mono-, di-, or tri-substituted alkylphenyl or alkylbenzyl group; and each substituent is a methyl, ethyl, propyl or butyl group, a methoxy group or a chlorine, fluorine or bromine atom.

3. A compound of claim 1, wherein X and Y are the same and are OH or NH$_2$ groups.

4. A compound of claim 1 selected from the group consisting of:
2,6-diamino-6,7-dihydro-6-methylpyrrolo[3,4-c]pyrido[2,3-d]-pyrimidine,
2,6-diamino-6,7-dihydro-6-ethylpyrrolo[3,4-c]pyrido[2,3-d]-pyrimidine,
2,6-diamino-6,7-dihydro-6-(n-propyl)pyrrolo[3,4-c]pyrido[2,3-d]-pyrimidine,
2,6-diamino-6,7-dihydro-6-(n-butyl)pyrrolo[3,4-c]pyrido[2,3-d]-pyrimidine,
2,6-diamino-6,7-dihydro-6-cyclopropylpyrrolo[3,4-c]pyrido[2,3-d]-pyrimidine,
2,6-diamino-6,7-dihydro-6-cyclopentylpyrrolo[3,4-c]pyrido[2,3-d]-pyrimidine,
2,6-diamino-6,7-dihydro-6-cyclohexylpyrrolo[3,4-c]pyrido[2,3-d]-pyrimidine,
2,6-diamino-6,7-dihydro-6-phenyl[3,4-c]pyrido[2,3-d]pyrimidine,
2,6-diamino-6,7-dihydro-6-(2-methoxyphenyl)pyrrolo[3,4-c]pyrido[2,3-d]-pyrimidine,
2,6-diamino-6,7-dihydro-6-(3-methoxyphenyl)pyrrolo[3,4-c]pyrido[2,3-d]-pyrimidine,
2,6-diamino-6,7-dihydro-6-(4-methoxyphenyl)pyrrolo[3,4-c]pyrido[2,3-d]-pyrimidine,
2,6-diamino-6,7-dihydro-6-(2,3-dimethoxyphenyl)-pyrrolo[3,4-c]pyrido[2,3-d]-pyrimidine,
2,6-diamino-6,7-dihydro-6-(2,4-dimethoxyphenyl)-pyrrolo[3,4-c]pyrido[2,3-d]-pyrimidine,
2,6-diamino-6,7-dihydro-6-(2,5-dimethoxyphenyl)-pyrrolo[3,4-c]pyrido[2,3-d]-pyrimidine,
2,6-diamino-6,7-dihydro-6-(3,4-dimethoxyphenyl)-pyrrolo[3,4-c]pyrido[2,3-d]-pyrimidine,
2,6-diamino-6,7-dihydro-6-(3,5-dimethoxyphenyl)-pyrrolo[3,4-c]pyrido[2,3-d]-pyrimidine,
2,6-diamino-6,7-dihydro-6-(3,4,5-dimethoxyphenyl)-pyrrolo[3,4-c]pyrido[2,3-d]-pyrimidine,
2,6-diamino-6,7-dihydro-6-(2-methylphenyl)pyrrolo[3,4-c]pyrido[2,3-d]-pyrimidine,
2,6-diamino-6,7-dihydro-6-(3-methylphenyl)pyrrolo[3,4-c]pyrido[2,3-d]-pyrimidine, 2,6-diamino-6,7-dihydro-6-(4-methylphenyl)pyrrolo[3,4-c]pyrido[2,3-d]-pyrimidine,
2,6-diamino-6,7-dihydro-6-(2,3-dimethylphenyl)pyrrolo[3,4-c]pyrido[2,3-d]-pyrimidine,
2,6-diamino-6,7-dihydro-6-(2,4-dimethylphenyl)pyrrolo[3,4-c]pyrido[2,3-d]-pyrimidine,
2,6-diamino-6,7-dihydro-6-(2,5-dimethylphenyl)pyrrolo[3,4-c]pyrido[2,3-d]-pyrimidine,
2,6-diamino-6,7-dihydro-6-(3,4-dimethylphenyl)pyrrolo[3,4-c]pyrido[2,3-d]-pyrimidine,
2,6-diamino-6,7-dihydro-6-(3,5-dimethylphenyl)pyrrolo[3,4-c]pyrido[2,3-d]-pyrimidine,
2,6-diamino-6,7-dihydro-6-(2,4,6-trimethylphenyl)-pyrrolo[3,4-c]pyrido[2,3-d]-pyrimidine,
2,6-diamino-6,7-dihydro-6-(2-fluorophenyl)pyrrolo[3,4-c]pyrido[2,3-d]-pyrimidine,
2,6-diamino-6,7-dihydro-6-(3-fluorophenyl)pyrrolo[3,4-c]pyrido[2,3-d]-pyrimidine,
2,6-diamino-6,7-dihydro-6-(4-fluorophenyl)pyrrolo[3,4-c]pyrido[2,3-d]-pyrimidine,
2,6-diamino-6,7-dihydro-6-(2-chlorophenyl)pyrrolo[3,4-c]pyrido[2,3-d]-pyrimidine,
2,6-diamino-6,7-dihydro-6-(3-chlorophenyl)pyrrolo[3,4-c]pyrido[2,3-d]-pyrimidine,
2,6-diamino-6,7-dihydro-6-(4-chlorophenyl)pyrrolo[3,4-c]pyrido[2,3-d]-pyrimidine,
2,6-diamino-6,7-dihydro-6-(2-bromophenyl)pyrrolo[3,4-c]pyrido[2,3-d]-pyrimidine,
2,6-diamino-6,7-dihydro-6-(3-bromophenyl)pyrrolo[3,4-c]pyrido[2,3-d]-pyrimidine,
2,6-diamino-6,7-dihydro-6-(4-bromophenyl)pyrrolo[3,4-c]pyrido[2,3-d]-pyrimidine,
2,6-diamino-6,7-dihydro-6-(2,3-difluorophenyl)pyrrolo[3,4-c]pyrido[2,3-d]-pyrimidine,
2,6-diamino-6,7-dihydro-6-(2,4-difluorophenyl)pyrrolo[3,4-c]pyrido[2,3-d]-pyrimidine,
2,6-diamino-6,7-dihydro-6-(2,5-difluorophenyl)pyrrolo[3,4-c]pyrido[2,3-d]-pyrimidine,
2,6-diamino-6,7-dihydro-6-(3,4-difluorophenyl)pyrrolo[3,4-c]pyrido[2,3-d]-pyrimidine,
2,6-diamino-6,7-dihydro-6-(3,5-difluorophenyl)pyrrolo[3,4-c]pyrido[2,3-d]-pyrimidine,
2,6-diamino-6,7-dihydro-6-(2,3-dichlorophenyl)pyrrolo[3,4-c]pyrido[2,3-d]-pyrimidine,
2,6-diamino-6,7-dihydro-6-(2,4-dichlorophenyl)pyrrolo[3,4-c]pyrido[2,3-d]-pyrimidine,
2,6-diamino-6,7-dihydro-6-(2,5-dichlorophenyl)pyrrolo[3,4-c]pyrido[2,3-d]-pyrimidine,
2,6-diamino-6,7-dihydro-6-(3,4-dichlorophenyl)pyrrolo[3,4-c]pyrido[2,3-d]-pyrimidine,
2,6-diamino-6,7-dihydro-6-(3,5-dichlorophenyl)pyrrolo[3,4-c]pyrido[2,3-d]-pyrimidine,
2,6-diamino-6,7-dihydro-6-(2,3-dibromophenyl)pyrrolo[3,4-c]pyrido[2,3-d]-pyrimidine,
2,6-diamino-6,7-dihydro-6-(2,4-dibromophenyl)pyrrolo[3,4-c]pyrido[2,3-d]-pyrimidine,
2,6-diamino-6,7-dihydro-6-(2,5-dibromophenyl)pyrrolo[3,4-c]pyrido[2,3-d]-pyrimidine,
2,6-diamino-6,7-dihydro-6-(3,4-dibromophenyl)pyrrolo[3,4-c]pyrido[2,3-d]-pyrimidine,
2,6-diamino-6,7-dihydro-6-(3,5-dibromophenyl)pyrrolo[3,4-c]pyrido[2,3-d]-pyrimidine,
2,6-diamino-6,7-dihydro-6-(2,4,6-trifluorophenyl)-pyrrolo[3,4-c]pyrido[2,3-d]-pyrimidine,
2,6-diamino-6,7-dihydro-6-(2,4,5-trifluorophenyl)-pyrrolo[3,4-c]pyrido[2,3-d]-pyrimidine,
2,6-diamino-6,7-dihydro-6-(3,4,5-trifluorophenyl)-pyrrolo[3,4-c]pyrido[2,3-d]-pyrimidine,
2,6-diamino-6,7-dihydro-6-(2,4,6-trichlorophenyl)-pyrrolo[3,4-c]pyrido[2,3-d]-pyrimidine,
2,6-diamino-6,7-dihydro-6-(2,4,5-trichlorophenyl)-pyrrolo[3,4-c]pyrido[2,3-d]-pyrimidine,
2,6-diamino-6,7-dihydro-6-(3,4,5-trichlorophenyl)-pyrrolo[3,4-c]pyrido[2,3-d]-pyrimidine,
2,6-diamino-6,7-dihydro-6-(2,4,6-tribromophenyl)-pyrrolo[3,4-c]pyrido[2,3-d]-pyrimidine,
2,6-diamino-6,7-dihydro-6-(2,4,5-tribromophenyl)-pyrrolo[3,4-c]pyrido[2,3-d]-pyrimidine,
2,6-diamino-6,7-dihydro-6-(3,4,5-tribromophenyl)-pyrrolo[3,4-c]pyrido[2,3-d]-pyrimidine,
2,6-diamino-6,7-dihydro-6-benzylpyrrolo[3,4-c]pyrido[2,3-d]-pyrimidine,
2,6-diamino-6,7-dihydro-6-(2-methoxybenzyl)pyrrolo[3,4-c]pyrido[2,3-d]-pyrimidine,
2,6-diamino-6,7-dihydro-6-(3-methoxybenzyl)pyrrolo[3,4-c]pyrido[2,3-d]-pyrimidine,
2,6-diamino-6,7-dihydro-6-(4-methoxybenzyl)pyrrolo[3,4-c]pyrido[2,3-d]-pyrimidine,
2,6-diamino-6,7-dihydro-6-(2,3-dimethoxybenzyl)-pyrrolo[3,4-c]pyrido[2,3-d]-pyrimidine,
2,6-diamino-6,7-dihydro-6-(2,4-dimethoxybenzyl)-pyrrolo[3,4-c]pyrido[2,3-d]-pyrimidine,
2,6-diamino-6,7-dihydro-6-(2,5-dimethoxybenzyl)-pyrrolo[3,4-c]pyrido[2,3-d]-pyrimidine,
2,6-diamino-6,7-dihydro-6-(3,4-dimethoxybenzyl)-pyrrolo[3,4-c]pyrido[2,3-d]-pyrimidine,
2,6-diamino-6,7-dihydro-6-(3,5-dimethoxybenzyl)-pyrrolo[3,4-c]pyrido[2,3-d]-pyrimidine,
2,6-diamino-6,7-dihydro-6-(2,4,5-trimethoxybenzyl)-pyrrolo[3,4-c]pyrido[2,3-d]-pyrimidine,
2,6-diamino-6,7-dihydro-6-(3,4,5-trimethoxybenzyl)-pyrrolo[3,4-c]pyrido[2,3-d]-pyrimidine,
2,6-diamino-6,7-dihydro-6-(2-methylbenzyl)pyrrolo[3,4-c]pyrido[2,3-d]-pyrimidine,
2,6-diamino-6,7-dihydro-6-(3-methylbenzyl)pyrrolo[3,4-c]pyrido[2,3-d]-pyrimidine,
2,6-diamino-6,7-dihydro-6-(4-methylbenzyl)pyrrolo[3,4-c]pyrido[2,3-d]-pyrimidine, and
2,6-diamino-6,7-dihydro-6-(2,5-dimethylbenzyl)pyrrolo[3,4-c]pyrido[2,3-d]-pyrimidine.

5. A compound of claim 1 selected from the group consisting of:
6-methyl-6,7-dihydropyrrolo[3,4-c]pyrido[2,3-d]pyrimidine-2,4(1H,3H)-dione,
6-ethyl-6,7-dihydropyrrolo[3,4-c]pyrido[2,3-d]pyrimidine-2,4(1H,3H)-dione,
6-(n-propyl)-6,7-dihydropyrrolo[3,4-c]pyrido[2,3-d]pyrimidine-2,4(1H,3H)-dione,
6(n-butyl)-6,7-dihydropyrrolo[3,4-c]pyrido[2,3-d]pyrimidine-2,4(1H,3H)-dione,
6-cyclopropyl-6,7-dihydropyrrolo[3,4-c]pyrido[2,3-d]pyrimidine-2,4(1H,3H)-dione,
6-cyclopentyl-6,7-dihydropyrrolo[3,4-c]pyrido[2,3-d]pyrimidine-2,4(1H,3H)-dione,
6-cyclohexyl-6,7-dihydropyrrolo[3,4-c]pyrido[2,3-d]pyrimidine-2,4(1H,3H)-dione,
6-cyclohexylmethyl-6,7-dihydropyrrolo[3,4-c]pyrido[2,3-d]pyrimidine-2,4(1H,3H)-dione,
6-phenyl-6,7-dihydropyrrolo[3,4-c]pyrido[2,3-d]pyrimidine-2,4(1H,3H)-dione,
6-(2-methoxyphenyl)-6,7-dihydropyrrolo[3,4-c]pyrido[2,3-d]pyrimidine-2,4(1H,3H)-dione,
6-(3-methoxyphenyl)-6,7-dihydropyrrolo[3,4-c]pyrido[2,3-d]pyrimidine-2,4(1H,3H)-dione,
6-(4-methoxyphenyl)-6,7-dihydropyrrolo[3,4-c]pyrido[2,3-d]pyrimidine-2,4(1H,3H)-dione, 6-(2,3-dimethoxyphenyl)-6,7-dihydropyrrolo[3,4-c]pyrido[2,3-d]pyrimidine-2,4(1H,3H)-dione,
6-(2,4-dimethoxyphenyl)-6,7-dihydropyrrolo[3,4-c]pyrido[2,3-d]pyrimidine-2,4(1H,3H)-dione,
6-(2,5-dimethoxyphenyl)-6,7-dihydropyrrolo[3,4-c]pyrido[2,3-d]pyrimidine-2,4(1H,3H)-dione,
6-(3,4-dimethoxyphenyl)-6,7-dihydropyrrolo[3,4-c]pyrido[2,3-d]pyrimidine-2,4(1H,3H)-dione,
6-(3,5-dimethoxyphenyl)-6,7-dihydropyrrolo[3,4-c]pyrido[2,3-d]pyrimidine-2,4(1H,3H)-dione,
6-(3,4,5-trimethoxyphenyl)-6,7-dihydropyrrolo[3,4-c]pyrido[2,3-d]pyrimidine-2,4(1H,3H)-dione,
6-(2-methylphenyl)-6,7-dihydropyrrolo[3,4-c]pyrido[2,3-d]pyrimidine-2,4(1H,3H)-dione,
6-(3-methylphenyl)-6,7-dihydropyrrolo[3,4-c]pyrido[2,3-d]pyrimidine-2,4(1H,3H)-dione,
6-(4-methylphenyl)-6,7-dihydropyrrolo[3,4-c]pyrido[2,3-d]pyrimidine-2,4(1H,3H)-dione,
6-(2,3-dimethylphenyl)-6,7-dihydropyrrolo[3,4-c]pyrido[2,3-d]pyrimidine-2,4(1H,3H)-dione,
6-(2,4-dimethylphenyl)-6,7-dihydropyrrolo[3,4-c]pyrido[2,3-d]pyrimidine-2,4(1H,3H)-dione,
6-(2,5-dimethylphenyl)-6,7-dihydropyrrolo[3,4-c]pyrido[2,3-d]pyrimidine-2,4(1H,3H)-dione,
6-(3,4-dimethylphenyl)-6,7-dihydropyrrolo[3,4-c]pyrido[2,3-d]pyrimidine-2,4(1H,3H)-dione,
6-(3,5-dimethylphenyl)-6,7-dihydropyrrolo[3,4-c]pyrido[2,3-d]pyrimidine-2,4(1H,3H)-dione,
6-(2,4,6-trimethylphenyl)-6,7-dihydropyrrolo[3,4-c]pyrido[2,3-d]pyrimidine-2,4(1H,3H)-dione,
6-(2-fluorophenyl)-6,7-dihydropyrrolo[3,4-c]pyrido[2,3-d]pyrimidine-2,4(1H,3H)-dione,
6-(3-fluorophenyl)-6,7-dihydropyrrolo[3,4-c]pyrido[2,3-d]pyrimidine-2,4(1H,3H)-dione,
6-(4-fluorophenyl)-6,7-dihydropyrrolo[3,4-c]pyrido[2,3-d]pyrimidine-2,4(1H,3H)-dione,
6-(2-chlorophenyl)-6,7-dihydropyrrolo[3,4-c]pyrido[2,3-d]pyrimidine-2,4(1H,3H)-dione,
6-(3-chlorophenyl)-6,7-dihydropyrrolo[3,4-c]pyrido[2,3-d]pyrimidine-2,4(1H,3H)-dione,
6-(4-chlorophenyl)-6,7-dihydropyrrolo[3,4-c]pyrido[2,3-d]pyrimidine-2,4(1H,3H)-dione,
6-(2,3-difluorophenyl)-6,7-dihydropyrrolo[3,4-c]pyrido[2,3-d]pyrimidine-2,4(1H,3H)-dione,
6-(2,4-difluorophenyl)-6,7-dihydropyrrolo[3,4-c]pyrido[2,3-d]pyrimidine-2,4(1H,3H)-dione,
6-(2,5-difluorophenyl)-6,7-dihydropyrrolo[3,4-c]pyrido[2,3-d]pyrimidine-2,4(1H,3H)-dione,
6-(3,4-difluorophenyl)-6,7-dihydropyrrolo[3,4-c]pyrido[2,3-d]pyrimidine-2,4(1H,3H)-dione,
6-(3,5-difluorophenyl)-6,7-dihydropyrrolo[3,4-c]pyrido[2,3-d]pyrimidine-2,4(1H,3H)-dione,
6-(2,3-dichlorophenyl)-6,7-dihydropyrrolo[3,4-c]pyrido[2,3-d]pyrimidine-2,4(1H,3H)-dione,
6-(2,4-dichlorophenyl)-6,7-dihydropyrrolo[3,4-c]pyrido[2,3-d]pyrimidine-2,4(1H,3H)-dione,
6-(2,5-dichlorophenyl)-6,7-dihydropyrrolo[3,4-c]pyrido[2,3-d]pyrimidine-2,4(1H,3H)-dione,
6-(3,4-dichlorophenyl)-6,7-dihydropyrrolo[3,4-c]pyrido[2,3-d]pyrimidine-2,4(1H,3H)-dione,
6-(3,5-dichlorophenyl)-6,7-dihydropyrrolo[3,4-c]pyrido[2,3-d]pyrimidine-2,4(1H,3H)-dione,
6-benzyl-6,7-dihydropyrrolo[3,4-c]pyrido[2,3-d]pyrimidine-2,4(1H,3H)-dione,
6-(2-methoxybenzyl)-6,7-dihydropyrrolo[3,4-c]pyrido[2,3-d]pyrimidine-2,4(1H,3H)-dione,
6-(3-methoxybenzyl)-6,7-dihydropyrrolo[3,4-c]pyrido[2,3-d]pyrimidine-2,4(1H,3H)-dione,
6-(4-methoxybenzyl)-6,7-dihydropyrrolo[3,4-c]pyrido[2,3-d]pyrimidine-2,4(1H,3H)-dione,
6-(2,3-dimethoxybenzyl)-6,7-dihydropyrrolo[3,4-c]pyrido[2,3-d]pyrimidine-2,4(1H,3H)-dione,
6-(2,4-dimethoxybenzyl)-6,7-dihydropyrrolo[3,4-c]pyrido[2,3-d]pyrimidine-2,4(1H,3H)-dione,
6-(2,5-dimethoxybenzyl)-6,7-dihydropyrrolo[3,4-c]pyrido[2,3-d]pyrimidine-2,4(1H,3H)-dione,
6-(3,4-dimethoxybenzyl)-6,7-dihydropyrrolo[3,4-c]pyrido[2,3-d]pyrimidine-2,4(1H,3H)-dione,
6-(3,5-dimethoxybenzyl)-6,7-dihydropyrrolo[3,4-c]pyrido[2,3-d]pyrimidine-2,4(1H,3H)-dione,
6-(2,4,5-trimethoxybenzyl)-6,7-dihydropyrrolo[3,4-c]pyrido[2,3-d]pyrimidine-2,4(1H,3H)-dione, and
6-(3,4,5-trimethoxybenzyl)-6,7-dihydropyrrolo[3,4-c]pyrido[2,3-d]pyrimidine-2,4(1H,3H)-dione.

* * * * *